United States Patent
Ji et al.

(10) Patent No.: US 8,718,106 B2
(45) Date of Patent: May 6, 2014

(54) NONLINEAR IMAGING USING PASSIVE PULSE SPLITTERS

(75) Inventors: Na Ji, Ashburn, VA (US); Eric Betzig, Ashburn, VA (US)

(73) Assignee: Howard Hughes Medical Institute, Chevy Chase, MD (US)

(*) Notice: Subject to any disclaimer, the term of this patent is extended or adjusted under 35 U.S.C. 154(b) by 0 days.

(21) Appl. No.: 13/099,475

(22) Filed: May 3, 2011

(65) Prior Publication Data

US 2011/0206075 A1 Aug. 25, 2011

Related U.S. Application Data

(62) Division of application No. 12/176,177, filed on Jul. 18, 2008, now Pat. No. 7,961,764.

(60) Provisional application No. 60/987,698, filed on Nov. 13, 2007, provisional application No. 60/971,792, filed on Sep. 12, 2007.

(51) Int. Cl.
*H01S 3/10* (2006.01)

(52) U.S. Cl.
USPC .............. 372/25; 359/586; 359/629; 359/633

(58) Field of Classification Search
USPC .......................................................... 372/25
See application file for complete search history.

(56) References Cited

U.S. PATENT DOCUMENTS

| 4,737,958 A | 4/1988 | Sizer, II |
| 4,772,085 A | 9/1988 | Moore et al. |
| 4,930,131 A | 5/1990 | Sizer, II |
| 5,034,613 A | 7/1991 | Denk et al. |
| 5,181,213 A | 1/1993 | Shinokura et al. |
| 5,296,960 A * | 3/1994 | Ellingson et al. ............. 359/330 |
| 5,316,983 A | 5/1994 | Fujimori |
| 5,337,333 A | 8/1994 | Daly et al. |
| 5,355,426 A | 10/1994 | Daniel et al. |
| 5,448,417 A | 9/1995 | Adams |

(Continued)

FOREIGN PATENT DOCUMENTS

JP 60-90443 5/1985

OTHER PUBLICATIONS

V. Narayan et al. "Design of Multimirror Structures for High-Frequency Bursts and Codes of Ultrashort Pulses" IEEE Journal of Quantum Electronics, vo. 30, No. 7, pp. 1671-1680 (1994).*

(Continued)

*Primary Examiner* — Xinning Niu
(74) *Attorney, Agent, or Firm* — DiBerardino McGovern IP Group LLC

(57) ABSTRACT

An apparatus includes a pulsed laser source that produces a pulsed laser beam at an input repetition rate and an input pulse power; a passive pulse splitter that receives the pulsed laser beam and outputs a signal including a plurality of sub-pulses for each input pulse of the pulsed laser beam, where the sub-pulses have a repetition rate that is greater than the input repetition rate and at least two of the sub-pulses have power less than the input pulse power; a sample accommodating structure configured to accommodate a sample placed in the path of a sample beam that is formed from the beam that exits the pulse splitter; and a detector that receives a signal of interest emitted from a sample accommodated by the sample accommodating structure based on the incident sample beam.

33 Claims, 20 Drawing Sheets

(56) References Cited

U.S. PATENT DOCUMENTS

| | | | |
|---|---|---|---|
| 5,479,431 | A | 12/1995 | Sobottke et al. |
| 5,644,666 | A | 7/1997 | Campbell et al. |
| 5,778,016 | A | 7/1998 | Sucha et al. |
| 6,166,385 | A | 12/2000 | Webb et al. |
| 6,366,356 | B1 | 4/2002 | Brosnan et al. |
| 6,521,899 | B1 | 2/2003 | Wolleschensky |
| 6,535,531 | B1 | 3/2003 | Smith et al. |
| 6,577,782 | B1 | 6/2003 | Leaird et al. |
| 6,697,196 | B2 | 2/2004 | Suzuki |
| 6,762,828 | B1 | 7/2004 | Duchenne et al. |
| 6,804,433 | B2 | 10/2004 | Takiguchi et al. |
| 6,920,263 | B2 | 7/2005 | Tadakuma et al. |
| 7,245,805 | B2 | 7/2007 | Alfano et al. |
| 7,298,545 | B2 * | 11/2007 | Kung et al. .......... 359/330 |
| 2001/0053008 | A1 | 12/2001 | Ueno |
| 2003/0012236 | A1 | 1/2003 | Hasson et al. |
| 2003/0123051 | A1 | 7/2003 | McGrew |
| 2003/0128923 | A1 | 7/2003 | Takiguchi et al. |
| 2003/0206292 | A1 | 11/2003 | Some |
| 2005/0226577 | A1 | 10/2005 | Alfano et al. |
| 2007/0047601 | A1 | 3/2007 | Yu |
| 2007/0171423 | A1 | 7/2007 | Namiki et al. |
| 2007/0215816 | A1 * | 9/2007 | Hui et al. .......... 250/458.1 |

OTHER PUBLICATIONS

P. Schlup et al. "Dispersion balancing of variable-delay monolithic pulse splitters" Optical Society of America, vol. 46, No. 23, pp. 5967-5973, Aug. 9, 2007.*

International Preliminary Report on Patentability, IPEA/US on Jul. 27, 2011 in counterpart application PCT/US08/70766, 12 pages.

P. Schlup et al., "Dispersion balancing of variable-delay monolithic pulse splitters," Optical Society of America, vol. 46, No. 23, pp. 5967-5973, 9 Au.

A.M. Weiner, "Femtosecond Pulse Shaping: Laser Machining and Frequency Conversion," Invited presentation at the 34th Winter Colloquium on the Physics of Quantum Electronics, Snowbird, UT, Jan. 5-8, 2004 (20 total pages).

Vishwa Narayan et al., "Design of Multimirror Structures for High-Frequency Bursts and Codes of Ultrashort Pulses," IEEE Journal of Quantum Electronics, vol. 30, No. 7, Jul. 1, 1994 (pp. 1671-1680).

Fittinghoff D. N. et al., "High-Efficiency Temporally Decorrelated Multifocal Arrays for Multiphoton Microscopy and Micromachining," Proceedings of the SPIE, SPIE, Bellingham, VA, US, vol. 4262, Jan. 21, 2001, pp. 202-209.

Jacinta Molloy, International Searching Authority, Notification of Transmittal of the International Search Report and Written Opinion of the International Searching Authority in related application PCT/US2008/070766, European Patent Office, mailed Apr. 2, 2009, 3 pages.

European Patent Office, Hermann Gnugesser, International Search Report in related application PCT/US2008/070766, mailed Apr. 2, 2009, 8 pages.

European Patent Office, Hermann Gnugesser, Written Opinion of the International Searching Authority in related application PCT/US2008/070766, mailed Apr. 2, 2009, 17 pages.

PCT Invitation to Pay Additional Fees including Search Report of International Application No. PCT/US2008/070766, dated Sep. 30, 2008, 8 pages.

* cited by examiner

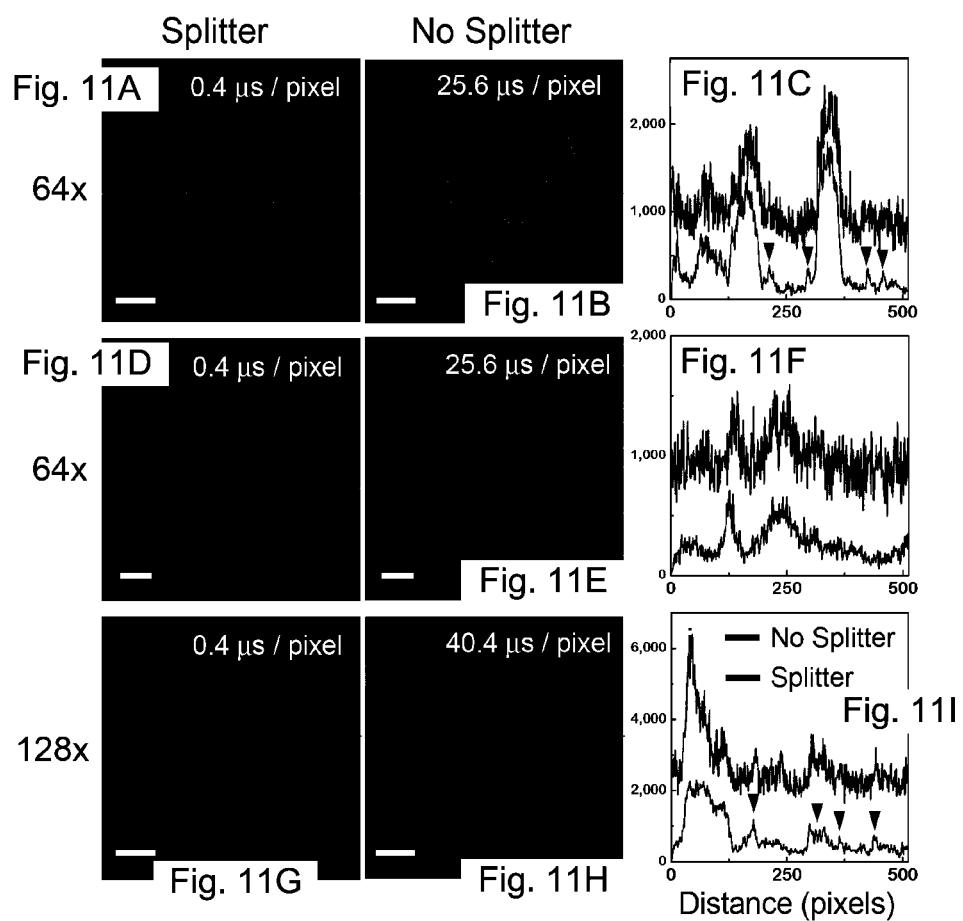

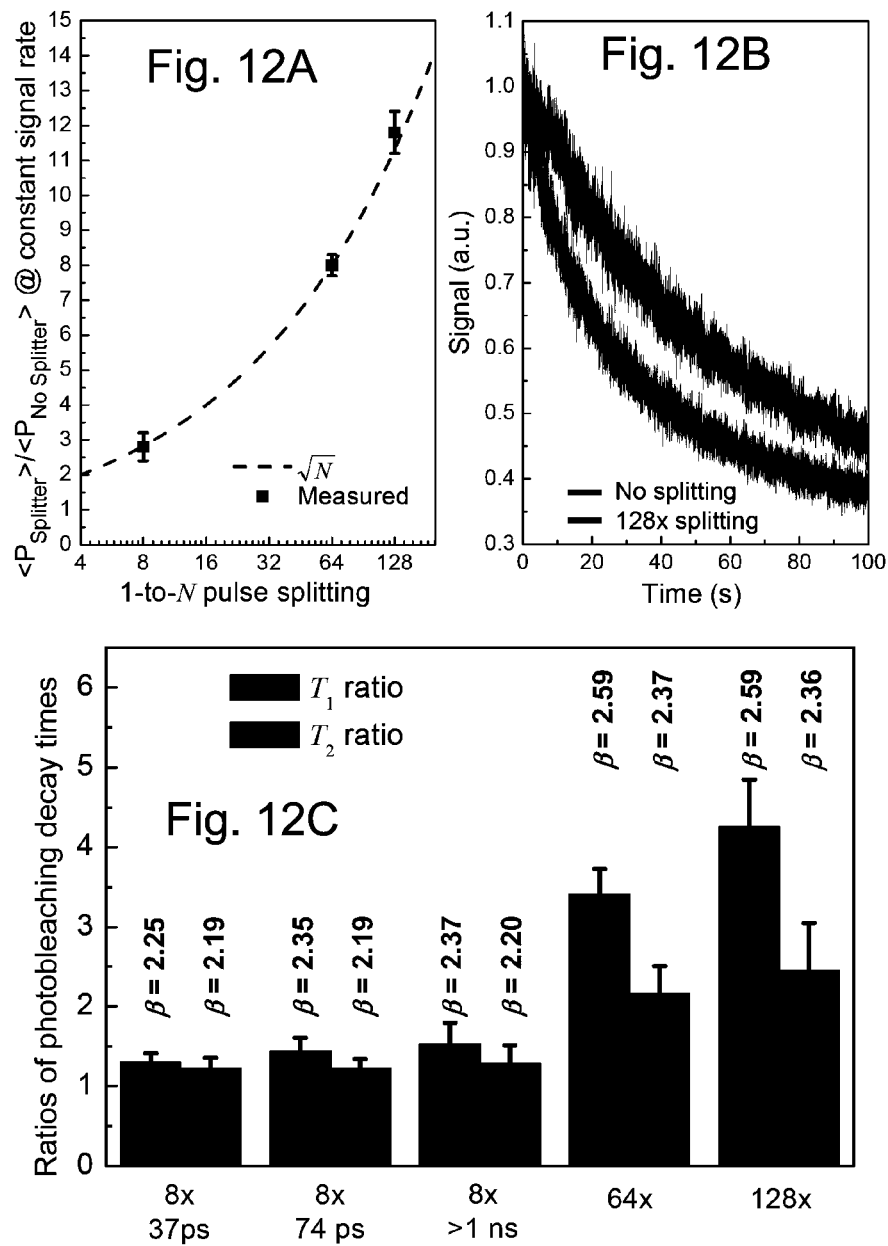

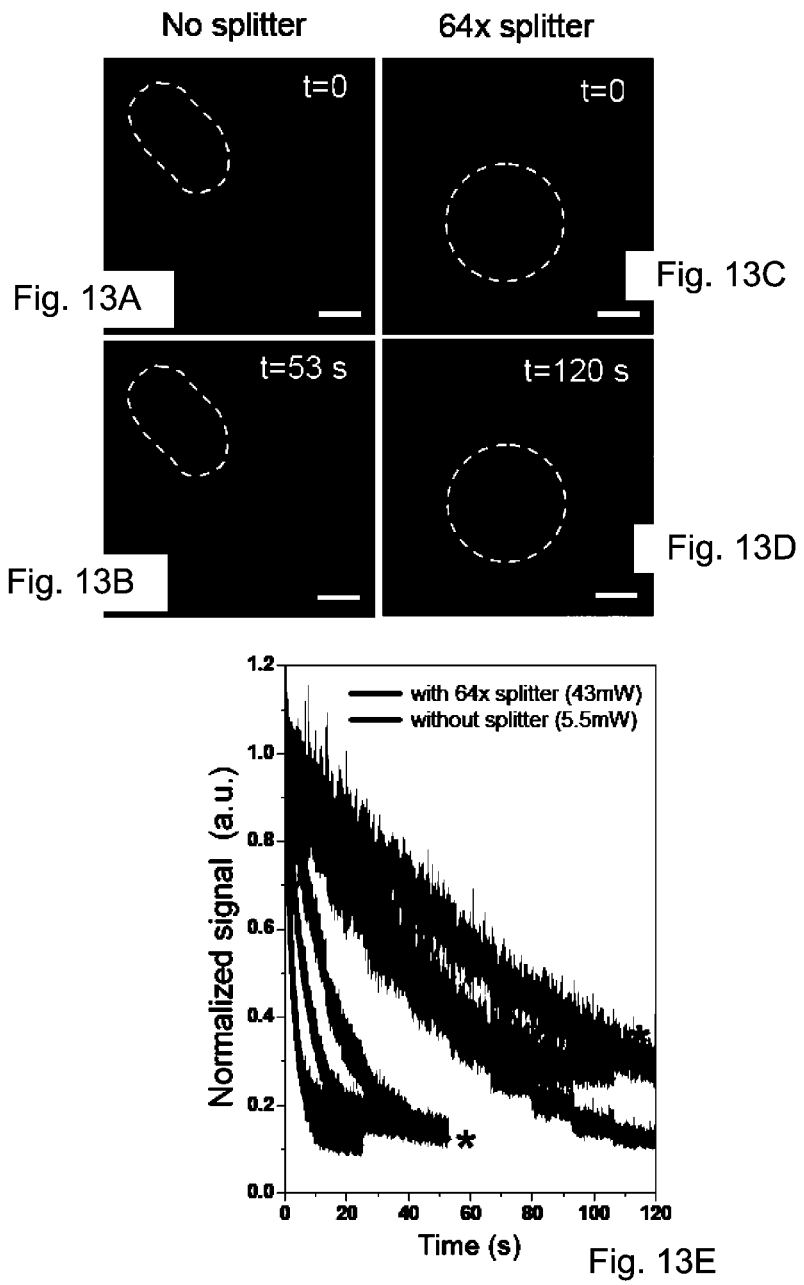

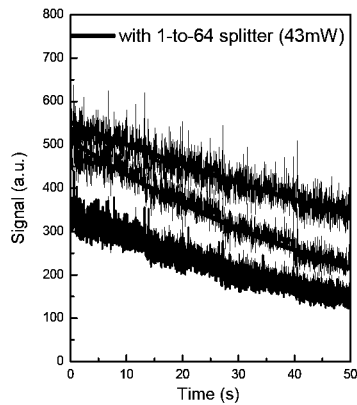
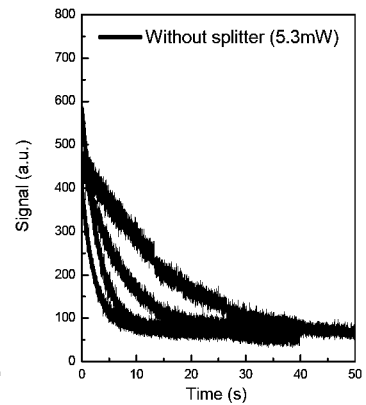
Fig. 14A    Fig. 14B
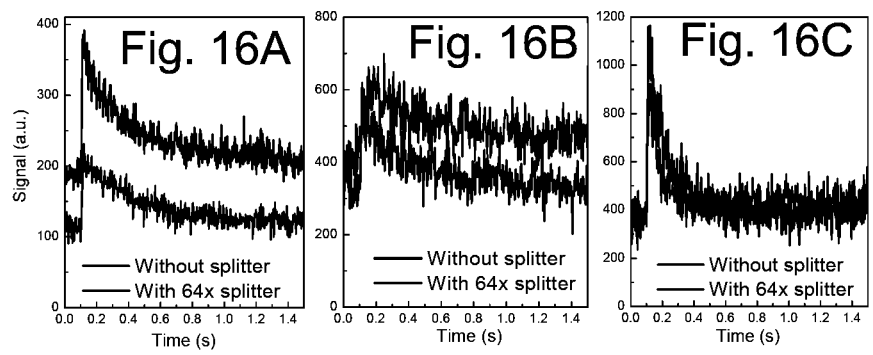

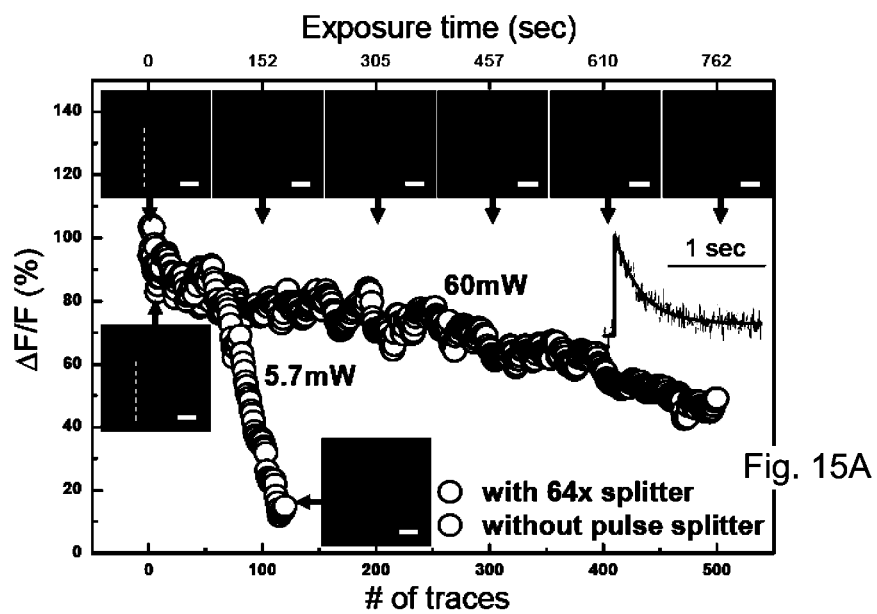
Fig. 15A
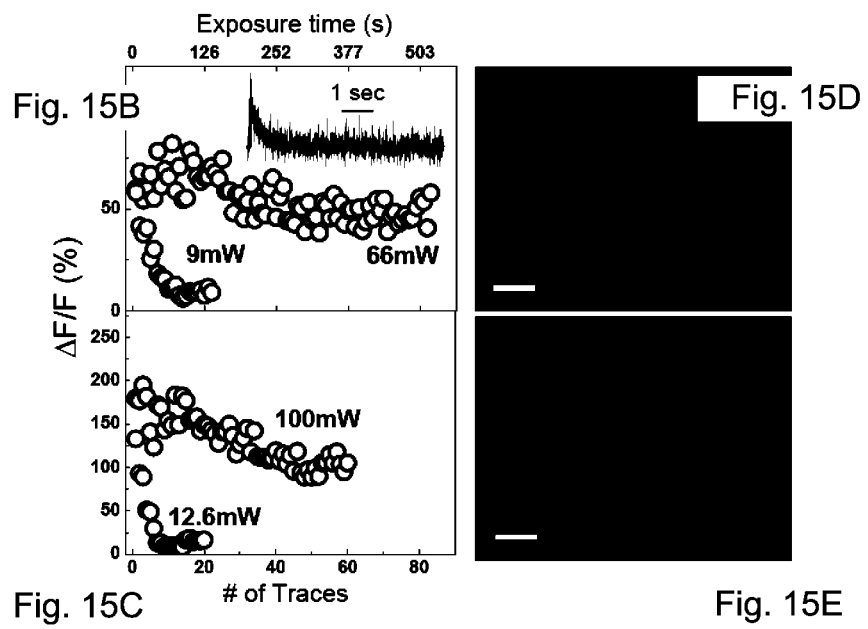
Fig. 15B
Fig. 15C
Fig. 15D
Fig. 15E

NONLINEAR IMAGING USING PASSIVE PULSE SPLITTERS

CROSS REFERENCE TO RELATED APPLICATION

This application is a divisional application of U.S. application Ser. No. 12/176,177, filed on Jul. 18, 2008, which claims the benefit of U.S. Application No. 60/987,698, filed on Nov. 13, 2007, and of U.S. Application No. 60/971,792, filed on Sep. 12, 2007. All of these applications are hereby incorporated by reference in their entirety.

TECHNICAL FIELD

The disclosure relates to passive pulse splitters and pulse splitter systems that include passive pulse splitters.

BACKGROUND

Pulsed lasers are used in nonlinear bio-imaging techniques such as multi-photon fluorescence excitation microscopy (MPFM) or two-photon fluorescence excitation microscopy (2PFM), which is a type of MPFM. In 2PFM, two photons of the same or different energy are absorbed by a molecule and the fluorescence from the molecule upon relaxation is collected with a highly sensitive detector such as a photomultiplier tube. Because the probability of near simultaneous absorption of two photons is low, a high flux of excitation photons is usually needed, and therefore an ultrafast (for example, femtosecond) pulsed laser is typically used. An example of a suitable pulsed light source is a Ti:sapphire laser, which can operate from 650-1100 nm with pulse widths of about 100-150 fs, repetition frequencies of about 70-80 MHz, and at several Watts of power (for example, 3 W).

SUMMARY

In some general aspects, a pulse splitting apparatus includes a pulsed laser source that produces laser pulses at an input repetition rate and an input pulse power, and a pulse splitter that receives the laser pulses from the pulsed laser source and outputs a plurality of sub-pulses for each laser pulse from the pulsed laser source. The sub-pulses have a repetition rate that is greater than the input repetition rate and the powers of the sub-pulses are less than the input pulse power. The pulse splitter includes at least two different materials through which the sub-pulses travel such that each of the sub-pulses travel along different optical path lengths through the different materials to cause a temporal separation between each of the sub-pulses. The optical path length depends on both the distance traveled through the material and the index of refraction of the material.

Implementations can include one or more of the following features. For example, the pulsed laser source can be a Ti-Sapphire laser. The pulsed laser source can produce time-averaged output powers of several Watts. The pulsed laser source can operate with an input repetition rate of about 70-80 MHz, a pulse width from about 10 fs to about 2 ps, and at a 650-1100 nm wavelength.

The pulse splitter can include one or more pairs of at least partly-reflecting surfaces that face each other, a first region between the one or more surface pairs and having a first refractive index and a first thickness, a second region between the one or more surface pairs and adjacent the first region, and having a second refractive index that is different from the first refractive index and a second thickness that is different from the first thickness, and a partially reflective interface between the first and second regions. The pulse splitter can output N sub-pulses for every one pulse input to the pulse splitter.

The pulse splitting apparatus can include a recombiner that receives the plurality of sub-pulses from the pulse splitter and recombines the sub-pulses to form a sub-pulse light source that is directed to a sample. The pulse splitting apparatus can include a delay external to the pulse splitter and through which at least some of the output of the pulse splitter is passed. The pulse splitting apparatus can include a motion stage to which the pulse splitter is attached such that the pulse splitter can be moved relative to the path that the laser pulses travel along.

The pulse splitter can be a passive pulse splitter.

The plurality of sub-pulses can be of equal or approximately equal intensity.

The pulse splitter can output the plurality of sub-pulses using substantially all of the available power from the pulsed laser source.

The pulse splitting apparatus can include a sample placed in the path of a sample beam that is formed from an output of the pulse splitter, and a detector that receives a multi-photon fluorescence signal emitted from the sample. The pulse splitting apparatus of claim 13, wherein the temporal separation between sub-pulses should be large enough to enable a molecule of the sample to relax to a lowest vibrational state of its excited state that is reached after multiple photons have been absorbed by the molecule.

Each of the sub-pulses can have a power that is less than the input pulse power. The repetition rate of the sub-pulses can vary.

In another general aspect, a method of pulse splitting includes producing a pulsed laser beam having a repetition rate and a pulse power, directing the pulsed laser beam into a pulse splitter that creates a finite number of sub-pulses for each input pulse of the pulsed laser beam by directing sub-pulses through at least two different materials and along different optical path lengths through the different materials to cause temporal separation between each of the sub-pulses. The pulse splitter produces an output signal that has a repetition rate that is greater than the repetition rate of the pulsed laser beam, and the powers of the sub-pulses are less than the pulse power of the pulsed laser beam.

Implementations can include one or more of the following features. For example, the pulsed laser source can be a Ti-Sapphire laser. The pulsed laser source can produce time-averaged output powers of several Watts. The pulsed laser source can operate with an input repetition rate of about 70-80 MHz, a pulse width from about 10 fs to about 2 ps, and at a 650-1100 nm wavelength.

The pulsed laser beam can be directed into the pulse splitter by directing the pulsed laser beam into a first region that is defined between first and second reflecting surfaces and has a first refractive index and a first thickness such that the laser beam travels through the first region and impinges upon a partially reflective interface between the first region and a second region adjacent the first region, and is split at the partially reflective interface, where the light that is reflected from the partially reflective interface strikes the first reflecting surface and any light that transmits through the partially reflective interface strikes the second reflecting surface. The pulse splitter can output N sub-pulses for every one pulse input to the pulse splitter and the partially reflective interface is configured to provide N passes or bounces of the light through the pulse splitter.

The method can include recombining the equal intensity sub-pulses output from the pulse splitter to form a sub-pulse light source that is directed to a sample. The method can include directing at least some of the sub-pulses output from the pulse splitter through a delay external to the pulse splitter. The method can include adjusting a position of the pulse splitter relative to the laser beam path.

The pulse splitter can produce the output signal without using external energy to act on the pulsed laser beam.

In another general aspect, a passive pulse splitter includes one or more pairs of at least partly-reflecting surfaces that face each other; a first region between the one or more surface pairs, the first region having a first refractive index and a first thickness; a second region between the one or more surface pairs, the second region being adjacent the first region, and having a second refractive index that is different from the first refractive index, a second thickness that is different from the first thickness, or both a second refractive index that is different from the first refractive index and a second thickness that is different from the first thickness; and a partially reflective interface between the first and second regions.

Implementations can include one or more of the following features. For example, the second region can be defined as an open air-filled region between the pair of at least partly-reflecting surfaces. The first region can be a fused silica substrate having a first surface that includes a coating that forms one of the at least partly-reflecting surfaces and having a second opposite surface that includes a coating that forms the partially reflective interface.

The partially reflective interface can include two or more segments of different reflectance. The partially reflective interface can include at least one segment that is 100% reflective.

In another general aspect, an apparatus includes a pulsed laser source that produces a pulsed laser beam at an input repetition rate and an input pulse power; a passive pulse splitter that receives the pulsed laser beam and outputs a signal including a plurality of sub-pulses for each input pulse of the pulsed laser beam, a sample placed in the path of a sample beam that is formed from the beam that exits the pulse splitter; and a detector that receives a signal of interest emitted from the sample. The output signal of the pulse splitter has a repetition rate that is greater than the input repetition rate and the powers of each of the sub-pulses are less than the input pulse power.

Implementations can include one or more of the following features. The detector can receive signals of interest from a plurality of locations at the sample to form an image. The signal of interest can be multi-photon fluorescence emitted from a nonlinear biological sample.

The pulsed laser source can be a Ti-Sapphire laser. The pulsed laser source can produce time-averaged output powers of several Watts. The pulsed laser source can operate with an input repetition rate of about 70-80 MHz, a pulse width from about 10 fs to about 2 ps, and at a 650-110 nm wavelength.

The signal of interest can be a second harmonic generation signal emitted from a nonlinear sample. The signal of interest can be a signal emitted from a nonlinear sample using coherent anti-Stokes Raman scattering spectroscopy with the output signal from the passive pulse splitter.

The pulse splitter can include one or more beam splitters and one or more beam couplers. The pulse splitter can include a plurality of waveguides.

The pulse splitter can include at least two different materials through which the sub-pulses travel such that each of the sub-pulses travel along different optical path lengths through different materials to cause temporal separation between each of the sub-pulses, wherein the optical path length depends on both the distance traveled through the material and the index of refraction of the material.

The pulse splitter can include one or more pairs of at least partly-reflecting surfaces that face each other; a first region between the one or more surface pairs and having a first refractive index and a first thickness; a second region between the one or more surface pairs and adjacent the first region, and having a second refractive index that is different from the first refractive index and a second thickness that is different from the first thickness; and a partially reflective interface between the first and second regions.

The pulse splitter can output N sub-pulses for every one pulse input to the pulse splitter.

The apparatus can include a recombiner that receives the plurality of sub-pulses from the pulse splitter and recombines the sub-pulses to form the sample beam. The apparatus can include a delay external to the pulse splitter and through which at least some of the output of the pulse splitter is passed. The apparatus can include a motion stage to which the pulse splitter is attached such that the pulse splitter can be moved relative to the path that the laser pulses travel along.

The plurality of sub-pulses can be of equal or approximately equal intensity.

The pulse splitter can output the plurality of sub-pulses using substantially all of the available power from the pulsed laser source.

In another general aspect, a signal detection method includes producing a pulsed laser beam having a repetition rate and a pulse power; directing the pulsed laser beam into a passive pulse splitter that creates a finite number of sub-pulses for each input pulse of the pulsed laser beam and produces an output signal that has a repetition rate that is greater than the repetition rate of the pulsed laser beam, directing a sample signal produced from the output signal of the pulse splitter to a sample; and directing a signal of interest emitted from the sample due to the interaction of the sample with the pulse splitter output to a detector. The powers of the sub-pulses are less than the pulse power of the pulsed laser beam;

Implementations can include one or more of the following features. For example, the method can include directing signals of interest from a plurality of locations at the sample to the detector to form an image. The method can include detecting the signal of interest emitted from the sample. The signal of interest emitted from the sample can be detected by detecting a fluorescence signal from the sample.

The method can include recombining sub-pulses from the pulse splitter output signal to form the sample signal. The method can include splitting the pulse splitter output signal into at least two signals and delaying at least one of the signals relative to the other signal.

The pulse splitter creates a finite number of sub-pulses from each input pulse, and does so with minimal or reduced power loss, so that the full power of the laser can be used to achieve larger (for example, greater than 100×) repetition rate gains at sub-pulse powers comparable to the single pulse powers currently used at the samples to be imaged. In some implementations, the sub-pulses can have equal or approximately equal powers. Such a design can be advantageous to prevent more powerful pulses from dominating the signal and causing photo-bleaching or damage. In other implementations, the sub-pulses can have different powers. Furthermore, the pulse splitter does not require undue manual alignment, even for the design in which the sub-pulses co-propagate to within about 10 arcsec in order for them to reach a common focal point within the sample, to obtain desired spatial resolution.

The pulse splitter is compact, requires few adjustments, and can be added to or retrofit to existing pulsed laser or microscope used in 2PFM without undue effort. The pulse splitter can be flexibly reconfigured to achieve desirable repetition rate, pulse spacing, and pulse intensity based on the photophysics of the system under investigation. The pulse splitter does not introduce unacceptable dispersion, permits repetition rate gains of at least 100×, and is adaptable to the large installed base of pre-existing lasers and 2PFM microscopes.

By coaxing higher signal rates from a single focus, the pulse splitter is well suited for data acquisition rates useful in a host of nonlinear optical applications including, but not limited to, neuroscience, and linear optical applications like Raleigh scattering or communications. If reduced photoinduced bleaching and damage is important, then pulse splitting using the pulse splitter can greatly increase the total integrated signal obtainable from various sample preparations, ranging from green fluorescent protein (GFP) in fixed tissues and living C. Elegans larvae, to $Ca^{2+}$ indicators in acute brain slices.

DESCRIPTION OF THE DRAWINGS

FIGS. 11A, 11D, and 11G are images of brain slices measured with a pulse splitter system and with different operational parameters;

FIGS. 11B, 11E, and 11H are images of brain slices measured without a pulse splitter system and with different operational parameters;

FIGS. 11C, 11F, and 11I are graphs showing comparative line profiles taken along the arrows shown at left images with a pulse splitter (in FIGS. 11A, 11D, and 11G) and center images without a pulse splitter (FIGS. 11B, 11E, and 11H);

FIG. 12A is a graph of a ratio of the average power to obtain a particular signal rate with and without a pulse splitter system;

FIG. 12B is a graph of photobleaching versus time with and without a pulse splitter system of GFP-labeled mouse brain slices;

FIG. 12C is a graph of summarized ratios of photobleaching decay times with and without a pulse splitter system for five different pulse splitter systems of FIGS. 9A-9E;

FIGS. 13A and 13B are images of muscle cells of GFP-labeled C. Elegans larva taken without a pulse splitter system at a time immediately following laser exposure (FIG. 13A) and at a time 53 s after laser exposure (FIG. 13B);

FIGS. 13C and 13D are images of muscle cells of GFP-labeled C. Elegans larva taken with a pulse splitter system of FIG. 9D at a time immediately following laser exposure (FIG. 13C) and at a time 120 s after laser exposure (FIG. 13D);

FIG. 13E is a graph of a normalized fluorescence signal versus time obtained with repeated line scans over single muscle cells with and without the pulse splitter system;

FIG. 14A is a graph of an un-normalized signal versus time obtained with the pulse splitter system of FIG. 9D;

FIG. 14B is a graph of an un-normalized signal versus time obtained without a pulse splitter system;

FIGS. 15A, 15B, and 15C are graphs of normalized fluorescence signal change versus number of traces and exposure time as measured from two dendritic branches of a single neuron, one with a pulse splitting system of FIG. 9D (the top green circles) and one without a pulse splitting system (the bottom grey circles);

FIGS. 15D and 15E are basal fluorescence images taken before (FIG. 15D) and after imaging (FIG. 15E) of the dendritic branches from which the data in FIGS. 15B and 15C, respectively, were obtained;

FIGS. 16A-16C are graphs of signal versus time for each series of traces of FIGS. 15A-15C, respectively;

DETAILED DESCRIPTION

A characteristic common to multi- or two-photon fluorescence microscopy (2PFM) measurements is the small excitation cross-sections involved, resulting in weak signals, long data acquisition times, and high requisite pulse powers. Furthermore, such signals cannot be increased arbitrarily by increasing pulse power, because in many cases photoinduced damage of the sample increases even faster with power. Thus, only a fraction of the laser power available can be delivered to the sample before photo-induced damage becomes excessive. For example, although most common ultrafast systems (that is, Ti:Sapphire laser systems) offer time-averaged output powers of several Watts, 2PFM imaging in a biological context is usually limited by photodamage to average powers of less than 10 mW at the sample, often yielding less than one detected photon per pulse, and wasting over 99% of the available laser power.

Figure 1:
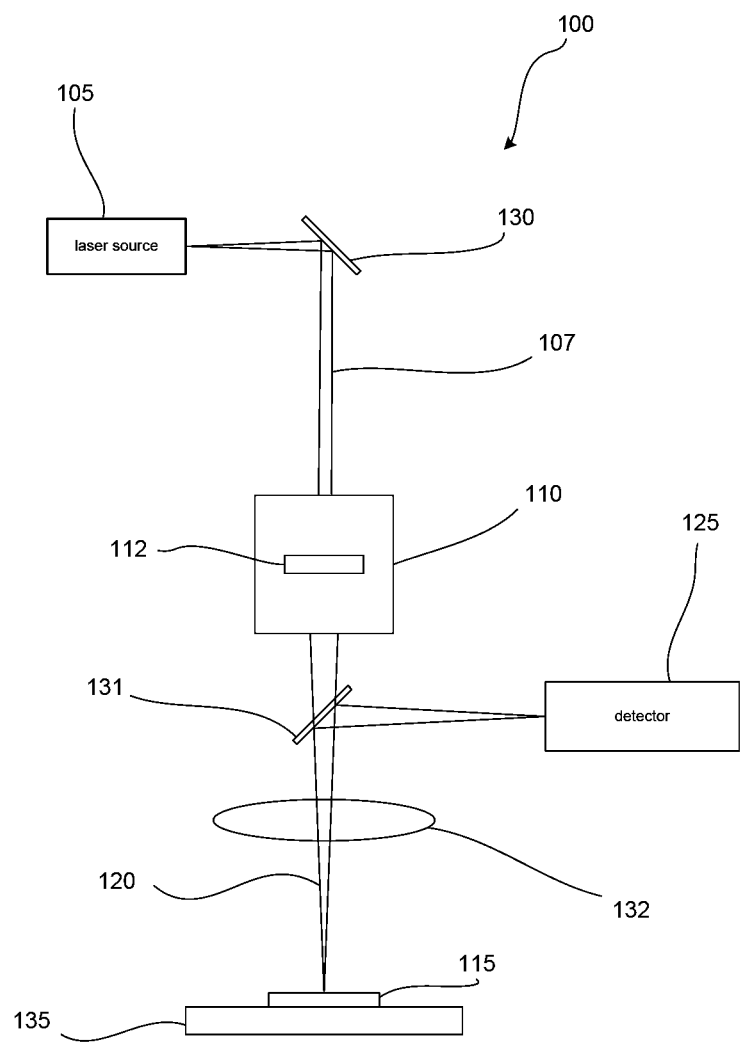
FIG. 1 is a block diagram of an imaging apparatus that includes a pulsed laser source that produces a pulsed laser beam.

Referring to FIG. 1, an imaging apparatus 100 includes at least one pulsed laser source 105 that produces a pulsed laser beam 107 at an input repetition rate and an input pulse power, an optical arrangement 110 that includes one or more passive pulse splitters 112, a nonlinear biological sample 115 to be imaged that is placed in the path of a beam 120 that exits the passive pulse splitter 110, and a detector 125 that receives a signal of interest emitted from the sample 115. The passive pulse splitter 112 receives the pulsed laser beam 107 from the laser source 105 or from another component within the optical arrangement 110, and outputs a signal including a plurality of equal or non-equal power sub-pulses for each input pulse of the pulsed laser beam 107, where the output signal has a repetition rate that is greater than the input repetition rate and the powers of the sub-pulses are less than the input pulse power. The apparatus 100 may also include other beam shaping and directing optics 130-132 for guiding the beams 107, 120 to the sample 115 or for guiding the signal to the detector 125 and the sample 115 can be mounted on a sample accommodating structure such as a suitable mount 135. Thus, the sample 115 can therefore receive the beam output directly from the pulse splitter 112 or can receive a sample beam that is formed from the beam that is output directly from the pulse splitter 112.

As discussed below, the passive pulse splitter 112 is designed to convert each laser pulse from the laser source 105 into a plurality of sub-pulses having equal, approximately equal, or unequal power, and the pulse splitter 112 can be designed to produce a particular sub-pulse repetition rate and a total number of sub-pulses. Thus, each of the sub-pulses can have a power that is similar to the powers of the other sub-pulses or the power of each of the sub-pulses can vary within a suitable range. Moreover, the repetition rate can vary along the train of the pulses within a suitable range. The pulse splitter 112 is "passive" in that it requires no active components that would use energy to act on the laser pulses. Examples of designs for the pulse splitter 112 are described below and shown in the remaining drawings.

To demonstrate its use, as discussed below, the pulse splitter 112 is applied to 2PFM imaging of fixed brain slices labeled with green fluorescent protein (GFP) and in different power regimes, the pulse splitter can either be used to increase the signal rate more than 100 fold, or to reduce the rate of photobleaching by over four-fold. In living specimens, the gains can be even greater: a nine-fold reduction in photobleaching during in vivo imaging of C. Elegans larvae; and a six to twenty-fold decrease in the rate of photodamage during functional calcium imaging of hippocampal brain slices.

One way to increase the signal rate and hence the speed of data acquisition N-fold is to accelerate the pulse repetition rate N-fold while maintaining the original pulse power. This can yield reduced photodamage compared to the approach of increasing the pulse power while maintaining the original repetition rate. In another limit, detailed below, the rate of photodamage at constant signal can be decreased by increasing pulse repetition rate, provided that the power per pulse is decreased appropriately.

Figure 2A:
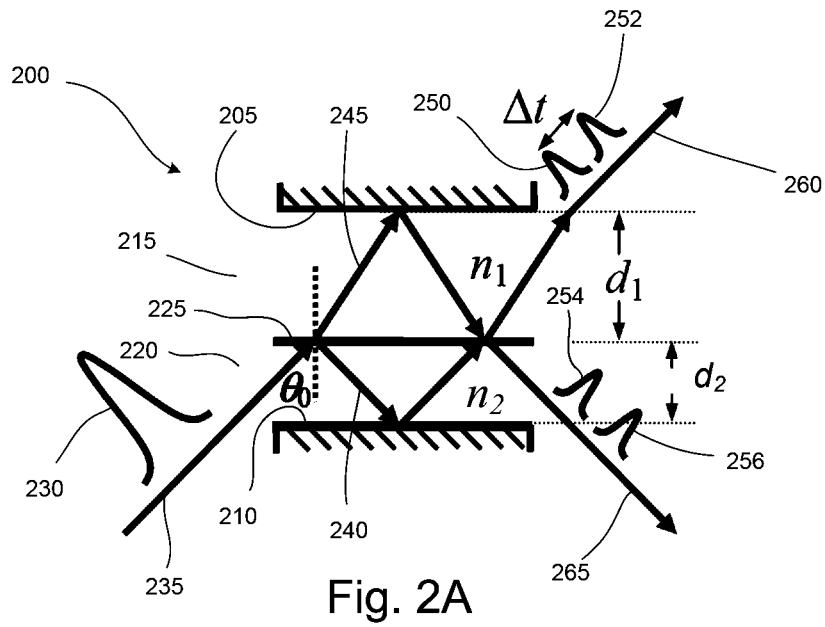
FIGS. 2A and 2B are top cross-sectional diagrams of a pulse splitter that can be used in the imaging apparatus of FIG. 1.

Referring to FIG. 2A, a pulse splitter 200 includes a pair of reflecting surfaces 205, 210 that are parallel with and face each other to define an internal opening. The reflecting surfaces 205, 210 can be planar to define a rectangular internal opening. The reflecting surfaces 205, 210 can be mirrored surfaces.

The pulse splitter 200 includes a first region 215 between the pair of reflecting surfaces 205, 210 and a second region 220 adjacent to the first region 215 and between the first region 215 and the reflecting surface 210. The first region 215 has a first refractive index $n_1$ and a first thickness $d_1$. The second region 220 has a second refractive index $n_2$ that is different from the first refractive index $n_1$ and a second thickness $d_2$ that is different from the first thickness $d_1$. The pulse splitter 200 includes a partially reflective interface 225 between the first and second regions 215, 220.

The regions 215, 220 are parallel with each other and are sandwiched between the two reflecting surfaces 205, 210. The partially reflective interface 225 can be a partially reflective coating applied to one or more of the materials that make up the regions 215, 220 at the interface between the two regions 215, 220.

In one implementation shown in FIG. 2A, an optical pulse 230 of a laser beam is directed along a path 235 into the region 220 of the pulse splitter 200 and at an incidence angle $\theta_0$ relative to the interface 225. The interface 225, in this implementation, is a 50% reflective interfacial coating. The optical pulse 230 is divided by the interface 225 into two optical pulses that are directed along paths 240, 245, each of these two optical pulses is divided again at the interface 225 after reflecting off of either the top or bottom surface 205, 210. Four optical sub-pulses 250, 252, 254, 256 exit the pulse splitter along paths 260, 265, with a pair of pulses emerging from just beyond each of the two reflecting surfaces 205, 210, where the sub-pulses within each path have an intra-pair pulse spacing $\Delta t$ of:

$$\Delta t = \frac{2}{c}\sqrt{(n_1^2 - n_2^2)(d_1^2 - d_2^2)},$$

where c is the speed of light. Moreover, sub-pulses emerging along the same path (either 260 or 265) are spatially overlapped if the incidence angle $\theta_0$ satisfies:

$$\cos\theta_0 = \frac{d_1}{n_1}\sqrt{\frac{n_1^2 - n_2^2}{d_1^2 - d_2^2}},$$

a condition that can be met even with loose tolerances on $d_1$, $d_2$ if the pulse splitter 200 is mounted on a rotational stage.

Figure 2B:
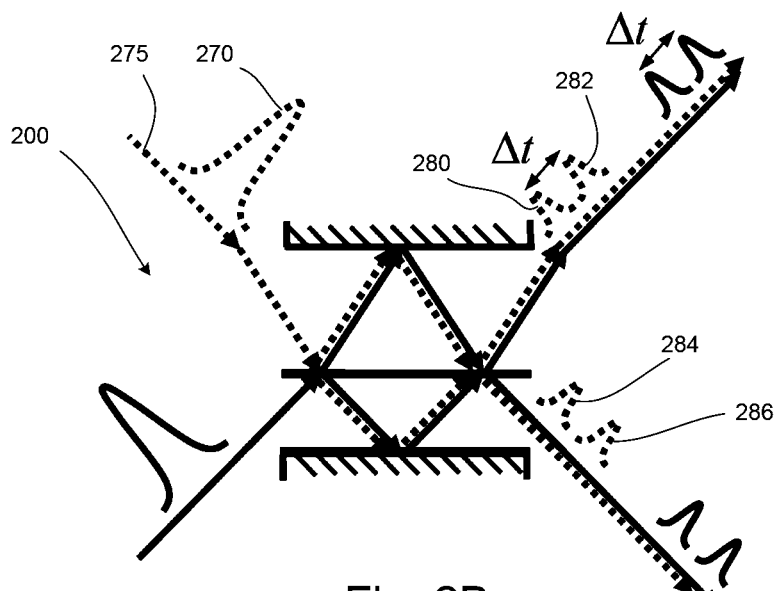

In another implementation shown in FIG. 2B, a second optical pulse 270 is directed along a path 275 into the region 215 of the pulse splitter 200 near the reflecting surface 205. In this way, four more sub-pulses 280, 282, 284, 286 can be created, where the sub-pulses 280, 282, 284, 286 exit along the paths 260, 265 as shown.

Figure 3A:
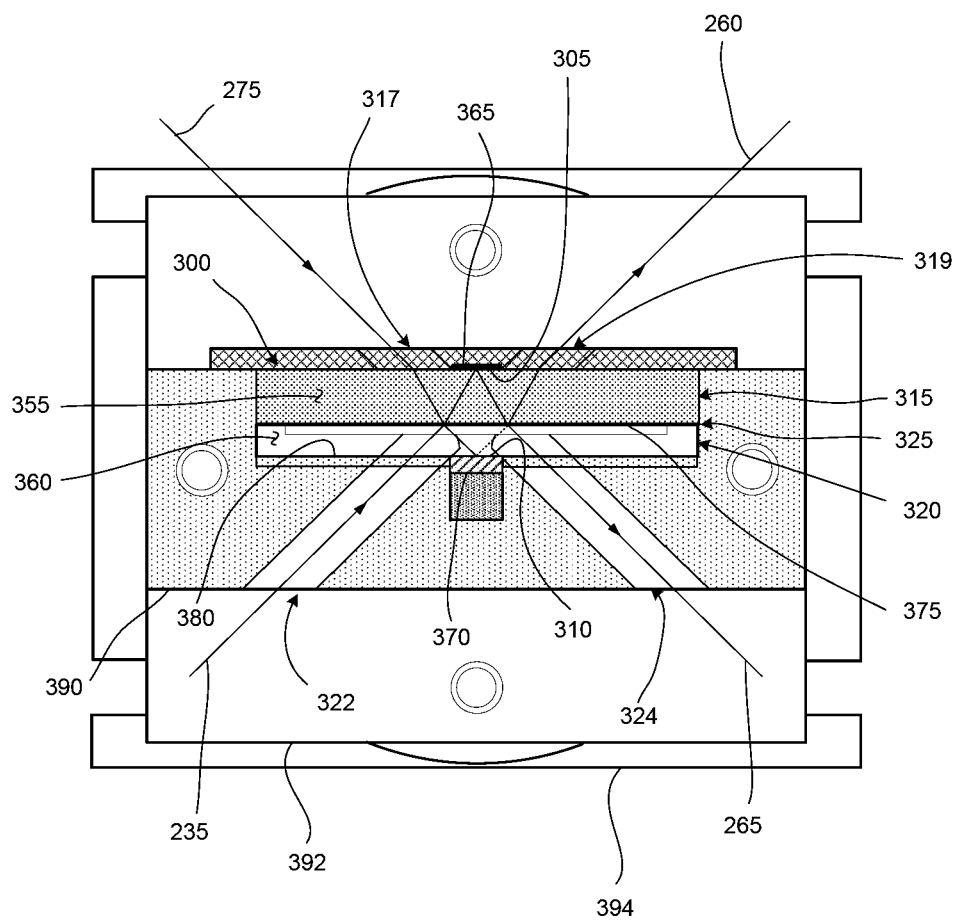
FIG. 3A is a top cross-sectional view of a pulse splitter that produces output pulses having an intra-pair pulse spacing of 37 ps and is designed based on the pulse splitter of FIGS. 2A and 2B.
Figure 3B:
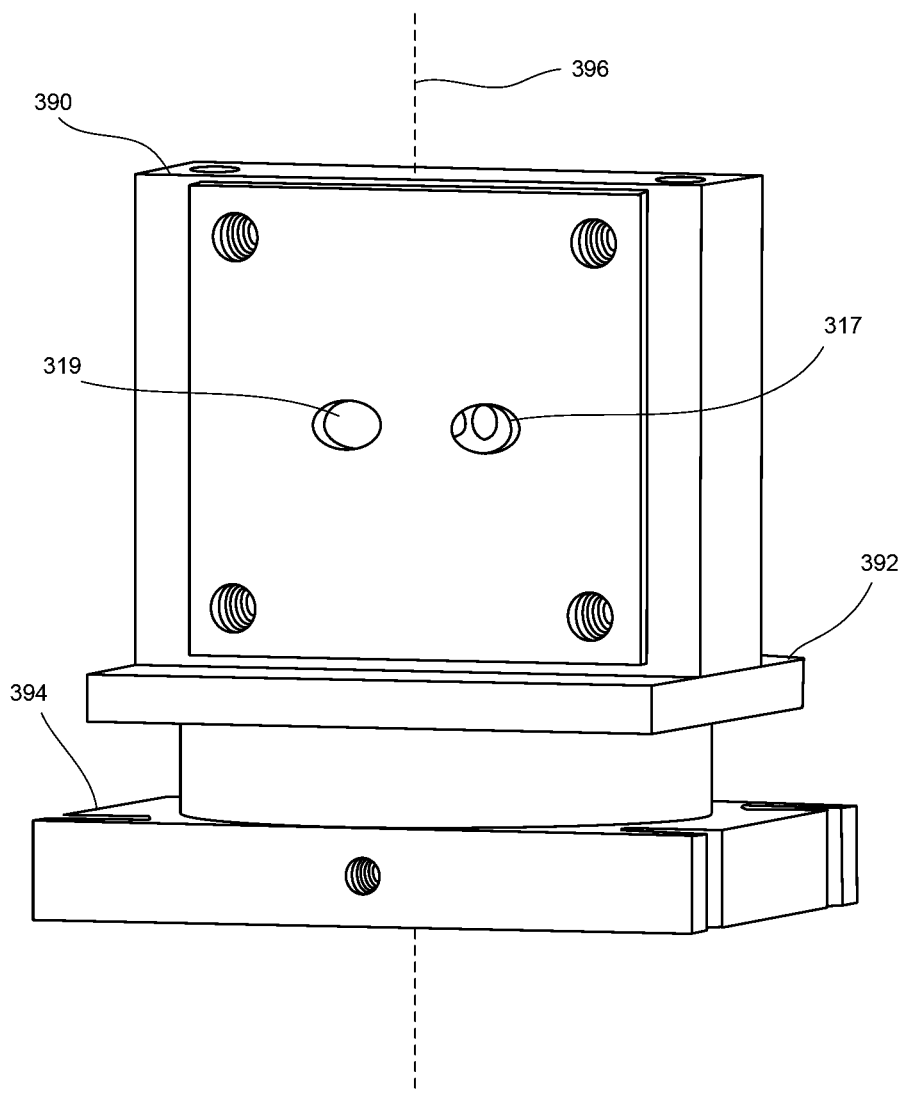
FIG. 3B is a side perspective view of the pulse splitter of FIG. 3A.

Referring to FIGS. 3A and 3B, a pulse splitter 300 is designed based on the principles discussed above with respect to FIGS. 2A and 2B. In the design shown in FIGS. 3A and 3B, the values of the refractive indices $n_1$ and $n_2$ and the values of the thicknesses $d_1$ and $d_2$ for regions 315, 320, respectively, have been selected to produce output pulses having an intra-pair pulse spacing $\Delta t$ of 37 ps.

The pulse splitter 300 is mounted in an optical holder 390 that is attached to a base 392 that is mounted on a motion (for example, a rotational) stage 394. The holder 390, the base 392, and the rotational stage 394 can be made of any suitable rigid material such as, for example, aluminum or stainless steel or a non-conductive material. The motion stage 394 can enable rotational movement of the base 392, the holder 390, and the pulse splitter 300 mounted to the holder 390 about an axis 396, and the motion stage 394 can also enable translational movement of the base 392, the holder 390, and the pulse splitter 300 in one or more directions.

The optical holder 390 includes input ports 317, 322 that are coupled to the regions 315, 320, respectively, to permit the passage of the pulses along the respective paths 275, 235 through the holder 390 and into the pulse splitter 300. The optical holder 390 also includes output ports 319, 324 that are coupled to the regions 315, 320, respectively, to permit the passage of the pulses along the respective paths 260, 265 out of the pulse splitter 300 and through the holder 390.

The holder 390 is designed with an internal cavity that is sized to receive the pulse splitter 300. In the design shown in FIGS. 3A and 3B, the region 315 is made of a substrate 355 having an index of refraction $n_1$ greater than 1 and the region 320 is a cavity 360 that is filled with air having an index of refraction $n_2$ equal to 1. Thus, for example, the substrate 355 is made of a fused silica substrate. In the implementation shown in FIGS. 3A and 3B, the reflecting surface 305 is formed on a top surface of the fused silica substrate 355 as a coating 365 that is fully reflective at the wavelength of the light from laser, and the reflecting surface 310 is formed as a separate mirror 370 that is placed at the bottom of the cavity 360. The coating 365 can be applied in a central region of the top surface of the substrate 355 and the surface surrounding the coating 365 can be either coated with an anti-reflecting coating or can be uncoated to allow the light to pass through the top surface of the substrate 355 along paths 275 and 260. Moreover, the partially reflective interface 325 is formed as a coating 375 on a bottom surface of the fused silica substrate 355.

The cavity 360 is defined between the bottom surface of the substrate 355 and an internal surface 380 of the holder 300 and the upper surface of the mirror 370. The substrate 355 can be separated from the internal surface 380 with a spacer (not shown) that is placed between the bottom surface of the substrate 355 and the internal surface 380 and the mirror 370, and the spacer is placed so that it does not interfere with the paths 260, 265, 275, 235. In some implementations, a biasing device such as a spring can be placed below the mirror 370 to bias the mirror 370 against the spacer, which pushes against the substrate 355, which pushes against the optical holder 390.

Figure 4A:
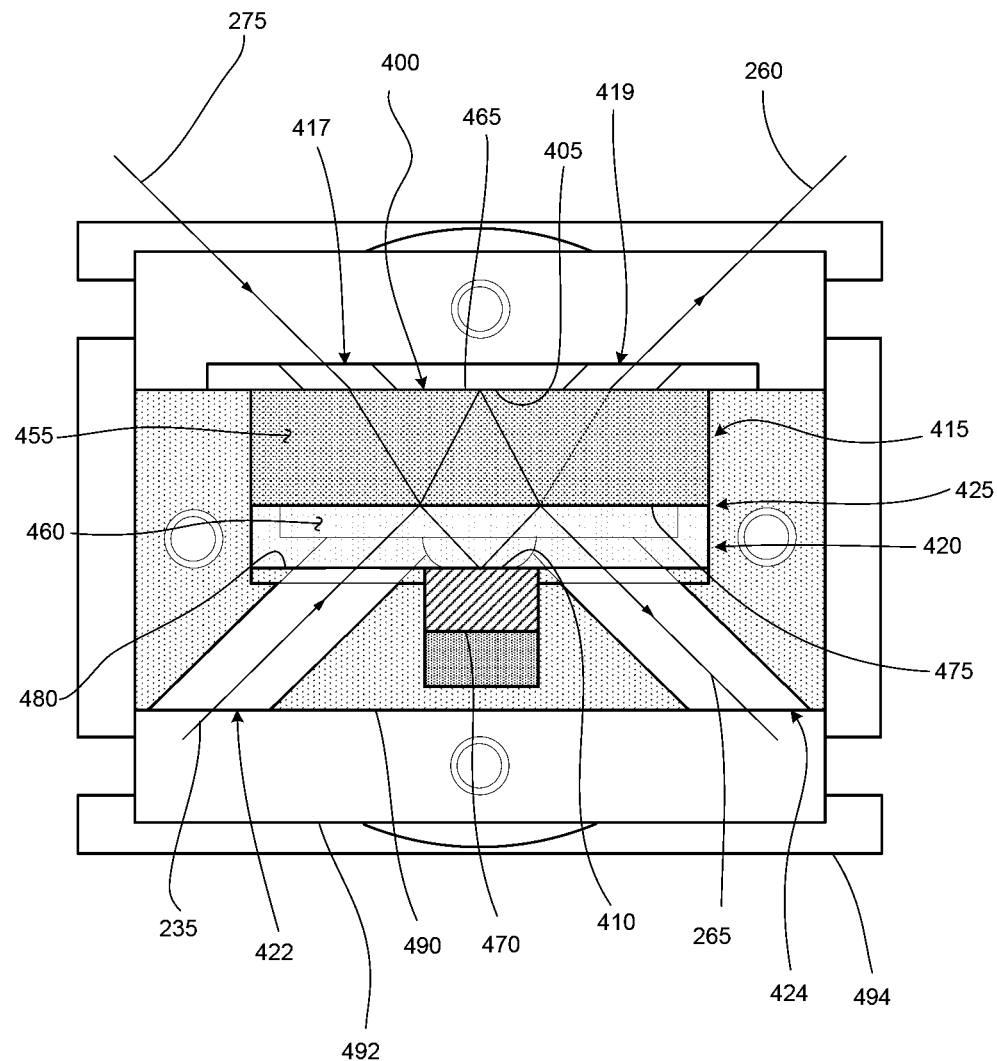
FIG. 4A is a top cross-sectional view of a pulse splitter that produces output pulses having an intra-pair pulse spacing of 74 ps and is designed based on the pulse splitter of FIGS. 2A and 2B.
Figure 4B:
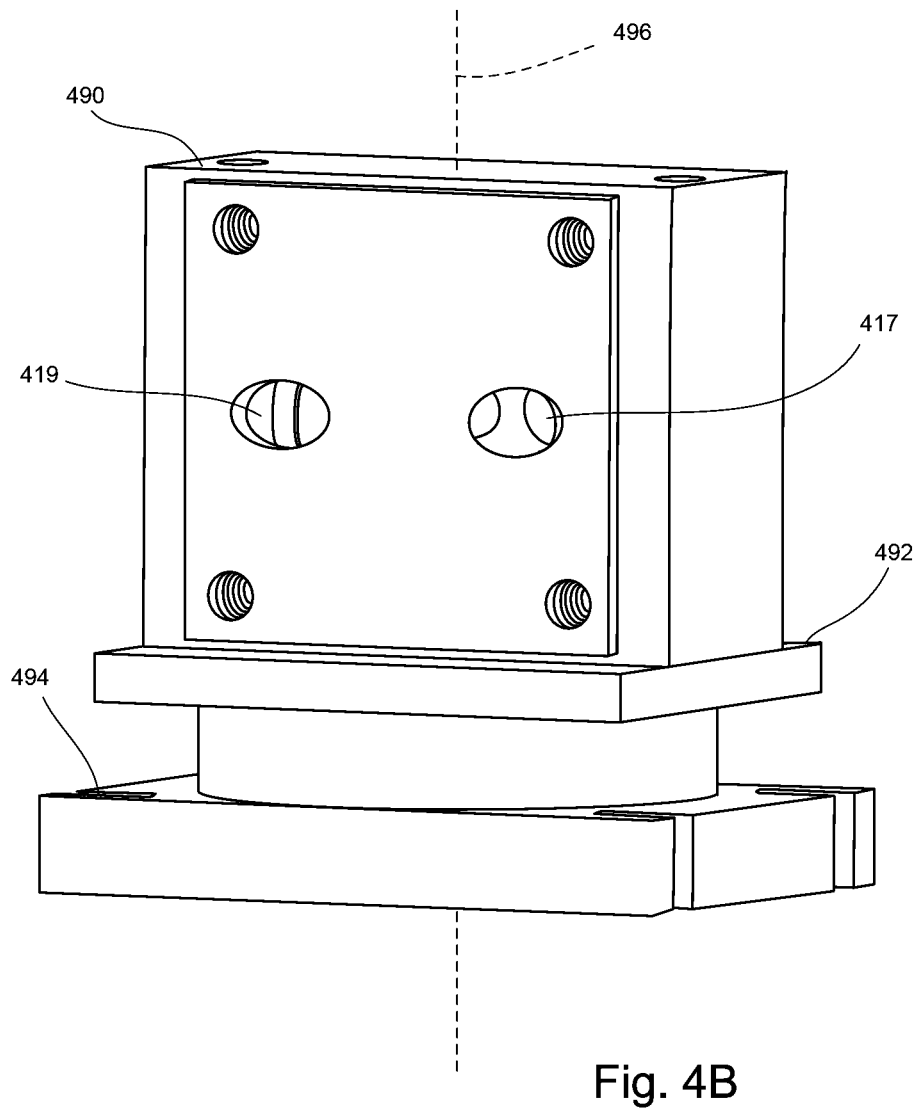
FIG. 4B is a side perspective view of the pulse splitter of FIG. 4A.

Referring also to FIGS. 4A and 4B, a pulse splitter 400 is designed based on the principles discussed above with respect to FIGS. 2A and 2B. In the design shown in FIGS. 4A and 4B, the values of the refractive indices $n_1$ and $n_2$ and the values of the thicknesses $d_1$ and $d_2$ for regions 415, 420, respectively, have been selected to produce output pulses having an intra-pair pulse spacing $\Delta t$ of 74 ps.

As with the pulse splitter 300, the pulse splitter 400 is also mounted in an optical holder 490 that is attached to a base 492 that is mounted on a motion (for example, a rotational) stage 494. The motion stage 494 enables rotational movement of the pulse splitter 400 about an axis 496, and the motion stage 494 can also enable translational movement of the pulse splitter 400 in one or more directions.

The optical holder 490 includes input ports 417, 422 that are coupled to the regions 415, 420, respectively, to permit the passage of the pulses along the respective paths 275, 235 through the holder 490 and into the pulse splitter 400. The optical holder 490 also includes output ports 419, 424 that are coupled to the regions 415, 420, respectively, to permit the passage of the pulses along the respective paths 260, 265 out of the pulse splitter 400 and through the holder 490.

The holder 490 has an internal cavity that is sized to receive the pulse splitter 400. The region 415 is made of a substrate 455 having an index of refraction $n_1$ greater than 1 and the region 420 is a cavity 460 that is filled with air having an index of refraction $n_2$ equal to 1. Thus, for example, the substrate 455 is made of a fused silica substrate. In the implementation shown in FIGS. 4A and 4B, the reflecting surface 405 is formed on a top surface of the fused silica substrate 455 as a coating 465 that is fully reflective at the wavelength of the light from laser and the reflecting surface 410 is formed as a separate mirror 470 that is placed at the bottom of the cavity 460. The coating 465 can be applied in a central region of the top surface of the substrate 455 and the surface surrounding the coating 465 can be either coated with an anti-reflecting coating or can be uncoated to allow the light to pass through the top surface of the substrate 455 along paths 275 and 260. Moreover, the partially reflective interface 425 is formed as a coating 475 on a bottom surface of the fused silica substrate 455.

The cavity 460 is defined between the bottom surface of the substrate 455 and an internal surface 480 of the holder 400. The substrate 455 can be separated from the internal surface 480 with a spacer (not shown) that is placed between the bottom surface of the substrate 455 and the internal surface 480 and the spacer is placed so that it does not interfere with the paths 260, 265, 275, 235. In some implementations, a biasing device such as a spring can be placed below the mirror 470 to bias the mirror 470 against the spacer, which pushes against the substrate 455, which pushes against the optical holder 490.

Figure 5A:
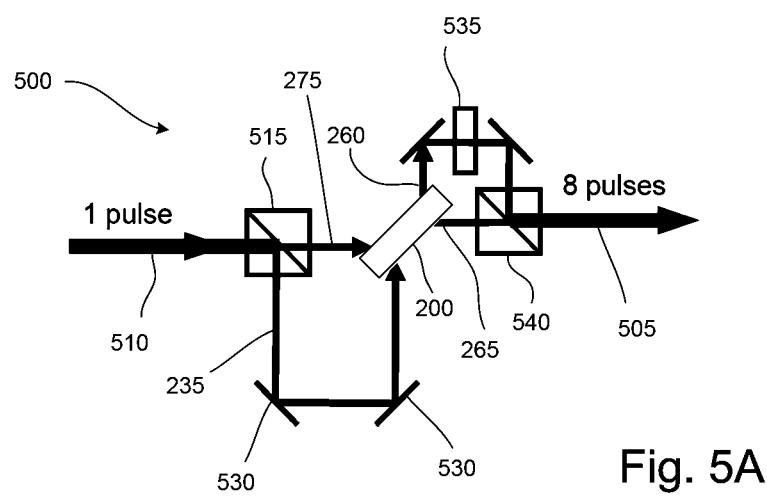
FIG. 5A is a diagram of a pulse splitter system including a pulse splitter that is designed based on the pulse splitter of FIGS. 2A and 2B.
Figure 5B:
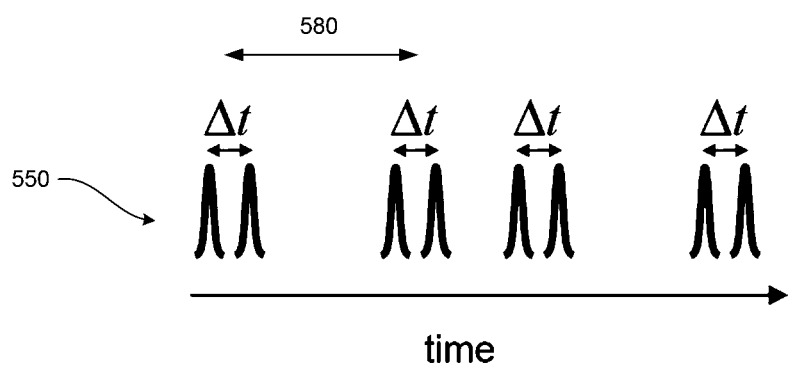
FIG. 5B is a diagram of a pulse shape output by the pulse splitter system of FIG. 5A.

Referring to FIG. 5A, the pulse splitter 200 (or the pulse splitters 300 or 400) can be used in an optical arrangement 500 that produces as an output eight pulses that travel along path 505 from one input pulse of the laser beam that travels along path 510. The arrangement 500 includes a beam splitter 515 that divides the input pulse into two pulses that travel along paths 235, 275. The pulse along path 235 is delayed relative to the pulse along path 275 using, for example, mirrors 530, and the two pulses are then directed to the pulse splitter 200. The sub-pulses 250, 252, 280, 282 and 254, 256, 284, 286 (not labeled in FIG. 5A) exit, respectively, along the paths 260, 265, and the pulses along path 260 (for example) are directed through a half-wave plate 535, and the pulses directed along both paths 260, 265 are directed through a polarizing beam splitter 540 to recombine the pulses into the common path 505. With appropriate delays, none of the eight pulses overlap in time, yielding a single output beam along path 505 that has a pulse train 550 shown in FIG. 5B and has an eight times higher repetition rate than the pulse directed along path 510. The inter-pulse delay time $\Delta t$ (the spacing in time between each pulse of the pair) is controlled by thicknesses $d_1$ and $d_2$ and the refractive indices $n_1$ and $n_2$ within the pulse splitter 200. Moreover, the separation between one pair of pulses and another pair of pulses is given by the lengths of the beam paths 235, 260, and 265. The inter-pair delay time 580 is controlled by the free-space propagation distance between the beam splitter 515 and the polarizing beam splitter 540.

Figure 6:
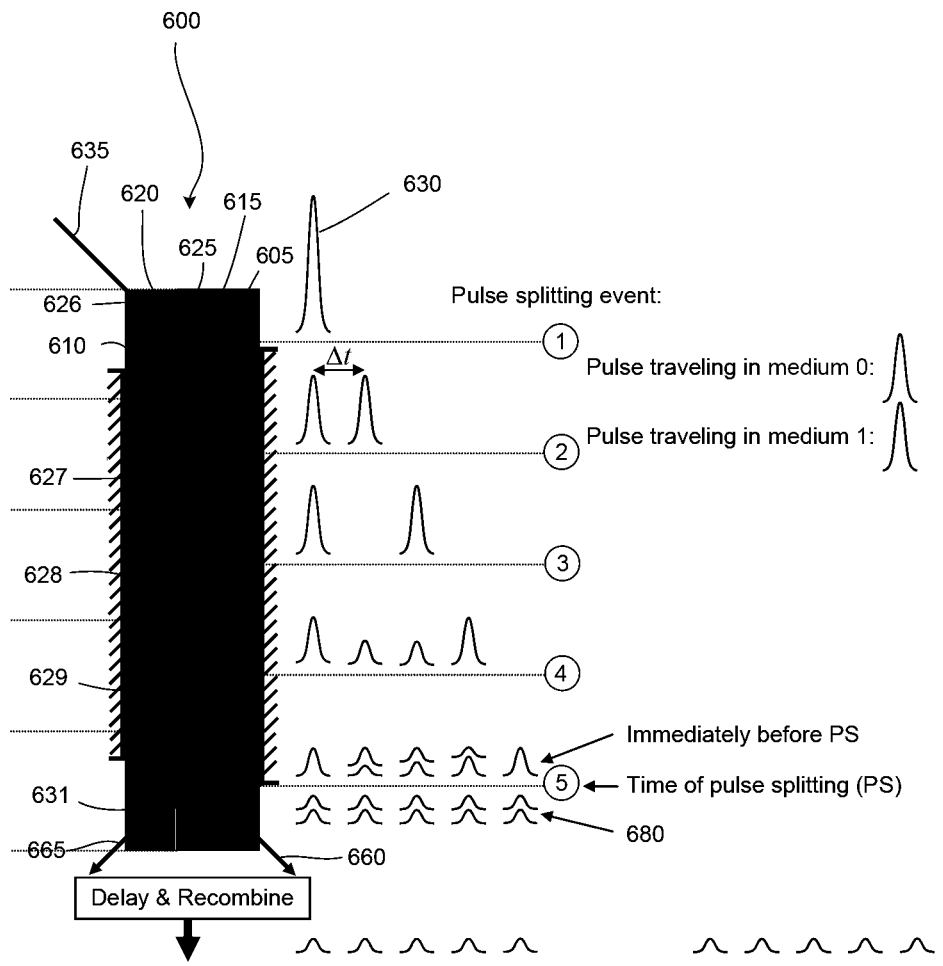
FIG. 6 is a top cross-sectional diagram of another implementation of a pulse splitter that is designed based on the pulse splitter described in FIGS. 2A and 2B.

Referring to FIG. 6, a monolithic pulse splitter 600 is designed to generate ten equal, approximately equal, or unequal power sub-pulses (having a pulse train 680) from a single pulse 630 input into the pulse splitter 600 along path 635. The pulse splitter 600 includes a pair of parallel reflecting surfaces 605, 610 that define an internal opening that houses a first region 615 and a second region 620. As with the design shown in FIGS. 2A and 2B, the first region 615 has a first refractive index $n_1$ and a first thickness $d_1$, and the second region 620 has a second refractive index $n_2$ that is different from the first refractive index $n_1$ and a second thickness $d_2$ that is different from the first thickness $d_1$.

The pulse splitter 600 includes a partially reflective interface 625 that is divided into segments 626, 627, 628, 629, 631 of varying reflectance. The reflectances of the segments 626, 627, 628, 629, 631 are selected to ensure that the output pulses emitted from the pulse splitter 600 are of the same power. Or, the reflectances of the segments 626, 627, 628, 629, 631 are selected to generate output pulse trains with specific patterns in the power output.

In the implementation of FIG. 6, five pulses are generated along each output path 660 and 665. The reflectance of segment 626 is 50%, the reflectance of segment 627 is 100%, the reflectance of segment 628 is 67%, the reflectance of segment 629 is 60%, and the reflectance of segment 631 is 50%. The pulse 630 is input through region 620 and impinges upon segment 626 of the interface 625 at $\hat{1}$, where the pulse 630 is split into two equal power sub-pulses, which are reflected off the surfaces 605, 610 and then directed to segment 627 of the interface 625 at $\hat{2}$, where the sub-pulses are completely reflected (because the segment 627 has a 100% reflectance). The sub-pulses reflected from the interface segment 627 are then reflected off the surfaces 605, 610 and then directed to segment 628 of the interface 625 at $\hat{3}$, where the sub-pulses are split with 67% of the power being reflected and 33% being transmitted through the segment 628. These four sub-pulses are reflected off the surfaces 605, 610 and then directed to segment 629 of the interface 625 at $\hat{4}$, where they are split with 60% of the power being reflected at the segment 629 and 40% being transmitted through the segment 629, thus resulting in eight sub-pulses. These eight sub-pulses are directed to the surfaces 605, 610, where they are reflected and directed toward the segment 631 of the interface 625 at $\hat{5}$.

The eight sub-pulses are split at segment 631 such that 50% of the power is reflected and 50% of the power is transmitted, and because of the time delay between the eight sub-pulses, some of the reflected and transmitted pulses overlap in time and result in ten equal-power sub pulses 680, five of which are output along path 660 and five of which are output along path 665.

Other reflectances can be used as long as the output pulses that travel along paths 660, 665 have approximately equal power, if the application dictates. The ten pulses generated along output paths 660, 665 (and shown in the pulse train 680) are then appropriately delayed and recombined, for example, using the setup shown in FIG. 5A.

In FIG. 6, the reflectance at the interface 625 is varied at each reflection point to produce output pulses having substantially equal power to achieve a balance between the signal and the photodamage that results when using the pulse splitter 600 in 2PFM. The reflectance at the interface 625 at each reflection point is varied so that the overall energy of each temporally overlapped pulse is equivalent to that of those pulses that remain temporally distinct. In this case, five reflections of one input pulse at the interface 625 lead to 10 output equal-energy sub-pulses.

Thus, in general, a pulse splitter can be designed to generate 2N pulses from each output port for a single input pulse, and such a pulse splitter is configured to provide N bounces or passes through the partially reflective interface. For N greater than two, the reflectance at a particular pass through the partially reflective interface may be different than the reflectances at other passes through the partially reflective interface to ensure that the powers of all output pulses are the same, if so desired. Moreover, a pulse splitter can be designed to produce $2^{N-1}$ pulses at each output port, such a pulse splitter has N regions of 50% reflectance (to split the pulses), interspersed with $2^{N-1}-N$ totally reflecting regions (to temporally separate otherwise overlapping pulses), as outlined in FIG. 7.

The term "splitting ratio" is used below to refer to the number of output pulses N produced relative to the number of input pulses, which can be by convention one. Thus, the "splitting ratio" is also the number of output pulses N for each single input pulse.

Figure 7:
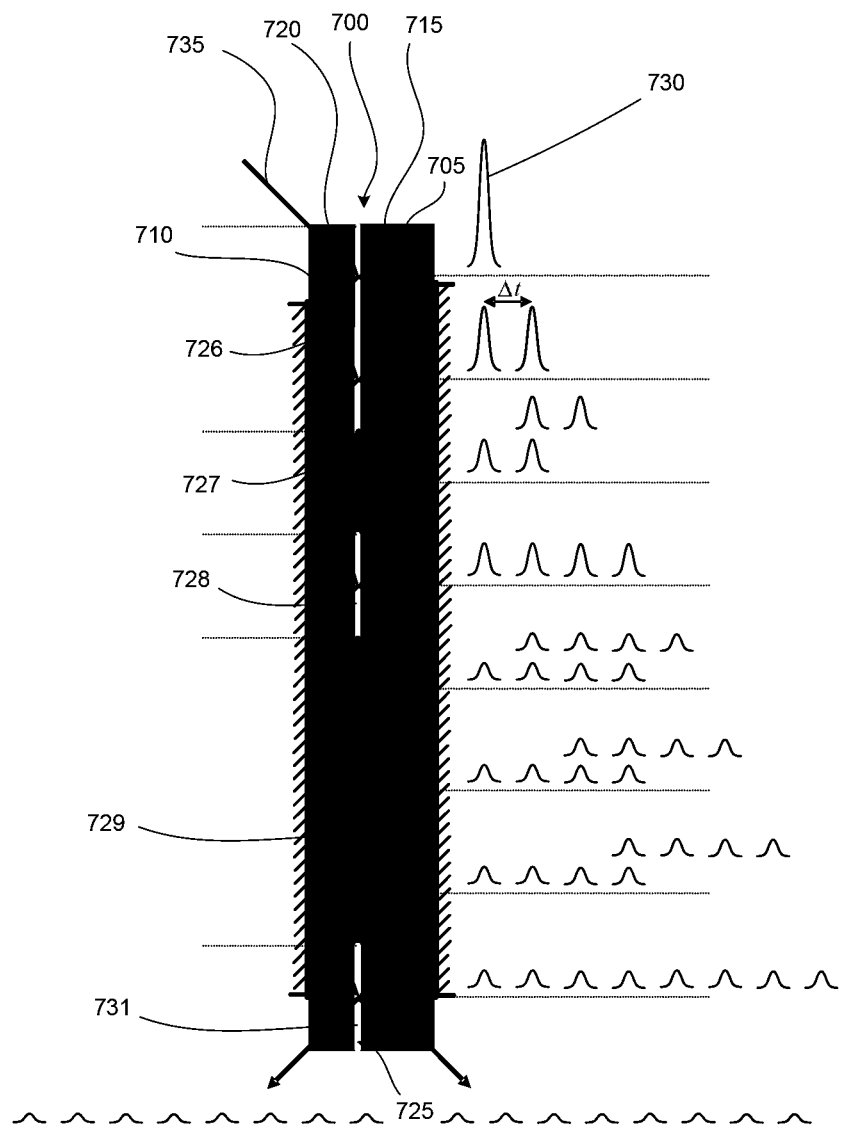
FIG. 7 is a top cross-sectional diagram of another implementation of a pulse splitter that is designed based on the pulse splitter described in FIGS. 2A and 2B.

Referring to FIG. 7, a pulse splitter 700 is designed to produce 16 equal or substantially-equal power sub-pulses from one pulse 730 input into the pulse splitter 700 along path 735. The pulse splitter 700 includes a pair of parallel reflecting surfaces 705, 710 that define an internal opening that houses a first region 715 and a second region 720. As with the design shown in FIGS. 2A and 2B, the first region 715 has a first refractive index $n_1$ and a first thickness $d_1$, and the second region 720 has a second refractive index $n_2$ that is different from the first refractive index $n_1$ and a second thickness $d_2$ that is different from the first thickness $d_1$.

The pulse splitter 700 includes a partially reflective interface 725 that is divided into segments 726, 727, 728, 729, 731 of varying reflectance. The reflectances of the segments 726, 727, 728, 729, 731 are selected to ensure that the output pulses emitted from the pulse splitter 700 are of the same or substantially the same power. In this case, the reflectance of each of the segments 726, 728, and 731 is 50% and the reflectance of each of the segments 727 and 729 is 100%. Thus, pulses that impinge upon segments 727 and 729 of the interface 725 are totally reflected at the interface 725.

In one implementation in which pulse splitting ratios of $2^N$ suffice (to enable 2PFM), it is possible to create output sub-pulses of equal power using N regions of 50% reflectance (such as segments 726, 728, 731), which split the pulse, and $2^{N-1}-N$ totally reflecting regions (such as segments 727, 729), which separate sub-pulses that would otherwise be temporally overlapped. Using only two interfacial coatings of differing reflectance considerably simplifies the fabrication of such pulse splitters.

With any of the pulse splitter geometries shown above, the arrangement of input and output beam splitters shown in FIG. 5A can be used to form a single input, single output pulse splitter of splitting ratio 4N or $2^{N+1}$.

The pulse splitters shown and described above rely on the differential optical path length to cause the sub-pulses to separate in time from each other. Another phenomenon that tends to work against this concept is, group-delay dispersion (GDD) within the materials internal to the pulse splitter and group-delay dispersion can lead to excessive sub-pulse broadening. The differential optical path length is the temporal pulse separation $\Delta t$ between the sub-pulses within the pulse splitter and it is arises because the sub-pulses travel along different path lengths in the upper and lower regions of the pulse splitter, due to the different thicknesses $d_1$, $d_2$ and the different refractive indices $n_1$, $n_2$ of the regions. The sub-pulses can therefore be separated using this phenomenon. The differential optical path length is given by the product of the actual path length L and the refractive index of the medium n. Moreover, to minimize or reduce group-delay dispersion while increasing the differential optical path length (and hence the number of sub-pulses N and/or their separation $\Delta t$), low dispersion fused silica ($n_1$=1.453 at 800 nm) and air ($n_2$=1) can be chosen for the respective regions 215, 220 of the pulse splitters. Other low dispersion materials can be used for region 215.

Separation of the sub-pulses is important when using the pulse splitter for MPFM or 2PFM, in which the temporal separation between sub-pulses should be greater than the time it takes for the molecule of the biological sample to relax from a higher vibrational state to its lowest vibrational state of its excited state. In particular, a molecule in the ground state absorbs the two photons from a first sub-pulse to reach the higher vibrational state. The probability that a given molecule will simultaneously absorb two photons is a function of both the spatial and temporal overlap between the incident photons within the sub-pulses. The next sub-pulse should arrive after the molecule has relaxed to its lowest vibrational state of its excited state, and the next sub-pulse may or may not arrive after the molecule has relaxed back down to the ground state. Thus, the temporal separation between the two sub-pulses should be large enough to enable the molecule to relax to a lowest vibrational state of the excited state.

Nevertheless, group-delay dispersion sets a practical limit on both N and $\Delta t$. For example, a pulse of 140 fs initial width (which is typical of commercial Ti:Sapphire lasers) broadens to about 240 fs if the group-delay dispersion of the pulse splitter is $10^4$ $fs^2$, and such group-delay dispersion corresponds to travel through a length L of about 50 cm of low dispersion fused silica. However, for the pulse splitters 200 and 600 of FIGS. 2A and 6, for example, that include input and output beam splitters 515, 540 as in FIG. 5A permitting both input ports of the pulse splitters to be used, the length L is related to N and $\Delta t$ by:

$$N \cdot \Delta t = \frac{4L}{c}\left(\frac{n_1^2 - n_0^2}{n_1}\right).$$

Thus, a useful figure-of-merit is that $N \cdot \Delta t$ is approximately 5.1 ns for a fused silica/air pulse splitter exhibiting $10^4$ $fs^2$ of group-delay dispersion. In other words, there is a trade-off between the number of sub-pulses output from the pulse splitter and their separation for a given degree of dispersion. In the case of an input pulse having a 140 fs initial width, the input pulse can be divided into 128 sub-pulses of less than or equal to 240 fs width separated by 40 ps each, or into 512 sub-pulses separated by 10 ps each. Furthermore, pulse broadening caused by group-delay dispersion decreases with increasing initial pulse width. Thus, in principle, pulse splitters can be designed for picosecond or longer pulsed sources with $N \cdot \Delta t$ being approximately 500 ns or more. In practice, however, N is limited by the tight tolerances required on the parallelism of the various reflective surfaces (for example, between reflecting surfaces 205, 210, and 225) within the pulse splitter (for example, the angle between two reflecting surfaces $\theta_{\infty}$ should be less than or equal to about 50/N arcsec)—a constraint necessary for all sub-pulses to reach the same focal point within the sample to be measured.

Figure 8:
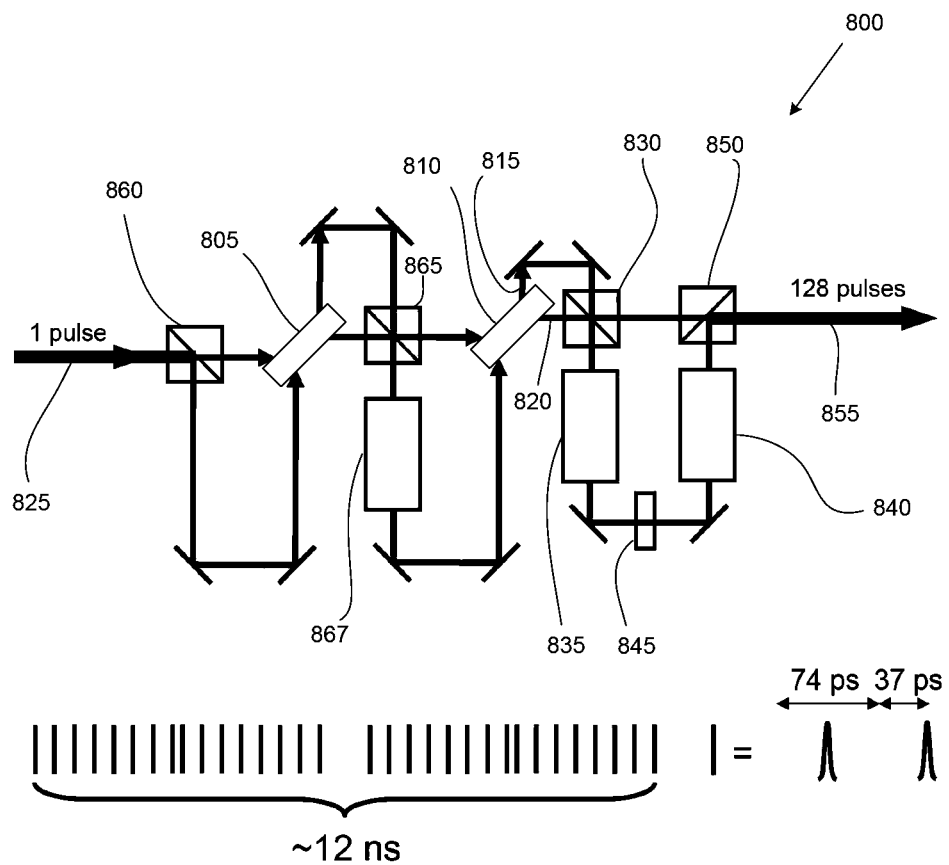
FIG. 8 is a diagram of a pulse splitter system including pulse splitters that are designed based on the pulse splitter of FIGS. 2A and 2B.

Thus, although a single monolithic pulse splitter having about 50 output pulses is within the capabilities of modern fabrication methods, a more modular approach is shown in FIG. 8, which shows a system 800 that relies on a serial arrangement of delay lines and pulse splitters 805, 810 each having smaller numbers N of output pulses and each having a different pulse spacing $\Delta t$. By adding or subtracting elements from the system 800, a different splitting ratio N may be obtained and the relationship between the signal and photobleaching could be better studied as a function of both the pulse repetition rate and the overall splitting ratio.

The system 800 in FIG. 8 includes the two splitters 805, 810 of pulse spacing $\Delta t=74$ ps and $\Delta t=37$ ps, respectively, that each produce four sub-pulses for every input pulse. Thus, for example, the pulse splitter 805 can be designed like the pulse splitter 400 of FIGS. 4A and 4B and the pulse splitter 810 can be designed like the pulse splitter 300 of FIGS. 3A and 3B.

The system 800 includes three 50%-50% beam splitters 860, 865, and 830 and three 2.5 ns delay lines 867, 835, and 840. The delay lines 867, 835, and 840 can be made, for example, by two reflecting surfaces positioned at opposite ends of a space so that a pulse that enters the delay line is reflected a plurality of times from the reflecting surfaces before exiting the delay line. The input pulse directed along path 825 is split by the beam splitter 860 into two beams, which are injected into both input ports of the pulse splitter 805, and the beam splitter 865 splits the beams emitted from the pulse splitter 805 into two beams, one of which is directed through the pulse delay 867, and then both beams are injected into both input ports of the pulse splitter 810. Thus, the second pulse splitter 810 receives the output pulses of the first pulse splitter 805, and 64 sub-pulses are produced along paths 815, 820 from the original input pulse directed along path 825. The output pulses along paths 815, 820 are directed through the beam splitter 830, the pulse delays 835, 840, and then recombined using a half wave plate 845 and a polarizing beam splitter 850 to produce 128 output sub-pulses directed along path 855, where the output sub-pulses are arranged in thirty-two groups of four pulses, with an intra-group spacing $\Delta t=37$ ps, distributed throughout the 12.5 ns interval between laser input pulses (for a laser with a 80 MHz repetition rate). By utilizing both input ports of each pulse splitter 805, 810, feeding 50% of each output from the pulse splitter 805 into each input of the pulse splitter 810, and by adding additional delay lines 867, 835, 840, 128 output sub-pulses can be produced covering several different time scales. The output pulse time sequence for the system 800 is shown below the diagram. Each vertical line in the sequence represents four pulses having an inter-pulse delay time of 37 ps.

The region 215 of the pulse splitter 805 can be a two-inch diameter fused silica plane parallel window having a thickness of about 0.5 inches that is sold by CVI Laser (part number PW1-2050-UV) and the region 115 of the pulse splitter 810 can be a two-inch diameter fused silica plane parallel window having a thickness of about 0.25 inches that is sold by CVI Laser (part number PW1-2025-UV). Each of these windows is custom-coated (by Reynard Corp.) with a 50% reflective dielectric coating over the entirety of one face that acts as the interface 225, and a greater than 98% reflective coating over a central circular region of the other face to form the reflecting surface 205, where the central circular region of the window used in the pulse splitter 805 has a 0.6 inch diameter and the central circular region of the window used in the pulse splitter 810 has a 0.3 inch diameter. Both coatings exhibited constant reflectivity over the 780-910 nm wavelength range typical of 2PFM. However, the coatings can be fabricated to work over a much broader range covering, for example, an entire Ti-sapphire spectrum. Protected silver mirrors of diameter 0.5 inch for pulse splitter 805 (purchased from Thorlabs, part number PF05-03-P01) and of diameter 0.28 inch for pulse splitter 810 (purchased from Thorlabs, part number PF03-03-P01) provided the bottom reflecting surfaces 210 of the pulse splitters 805, 810, respectively.

Precision ground spacers of thickness 0.28 inch (for the pulse splitter 805) and 0.14 inch (for the pulse splitter 810) were used to position each mirror that provides the bottom reflecting surfaces 210 (such as, for example, mirrors 470 and 370) with respect its corresponding fused silica plane parallel window that provides the top reflecting surfaces 205, thereby creating the air gap that served as the region 220 within each of the pulse splitters 805, 810. With these gap dimensions, sub-pulses emerging from both output ports of each pulse splitter 805, 810 were nominally spatially concentric at an input beam incident angle of 45°. In practice, each pulse splitter is mounted on a rotational stage (that can be purchased from Thorlabs, part number PR01) to optimize the overlap of all output beams such as shown in FIGS. 3A, 3B, 4A, and 4B.

The non-polarizing beam splitter 860 can be purchased from Thorlabs (part number BS011), and the non-polarizing beam splitters 865 and 830 can be purchased from Thorlabs (part numbers BS011, BS017, respectively). The half-wave plate 845 can be purchased from CASIX (part number WPA1312-λ/2-700 nm-1000 nm) or from Thorlabs, and the polarizing beam splitter 850 can be purchased from Newport (part number 10FC16PB.5). The three 2.5 ns delay lines 867, 835, 840 each consisted of opposed high-reflectivity (great than about 99.8%) low-dispersion mirrors (Precision Photonics Corp, MI1000-TiD) separated by a 4.0 inch spacer. Pulses traveled three round trips between these mirrors before emerging. Moreover, the greatest pulse separation occurred along the path from the beam splitter 830 through the delay lines 835 and 840, and to the beam splitter 850.

The pulse splitter system 800 and design is structurally stable; after an initial alignment, no re-alignment was needed over weeks of operation.

Figure 9A:
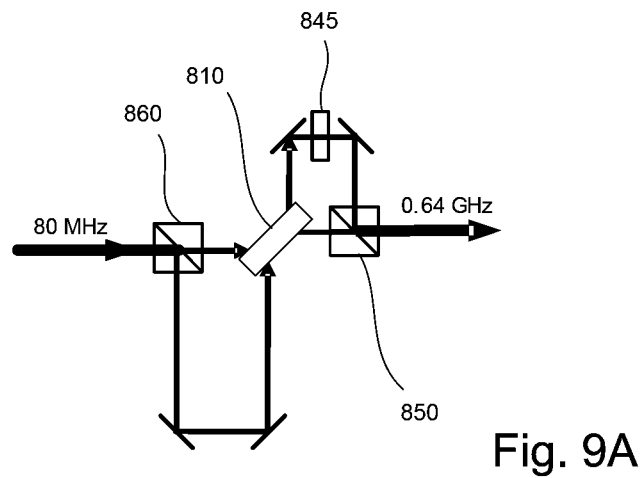
FIGS. 9A-9E are diagrams of pulse splitter systems.
Figure 9B:
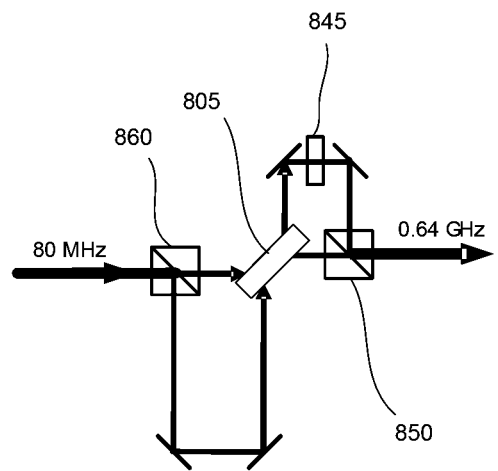
Figure 9C:
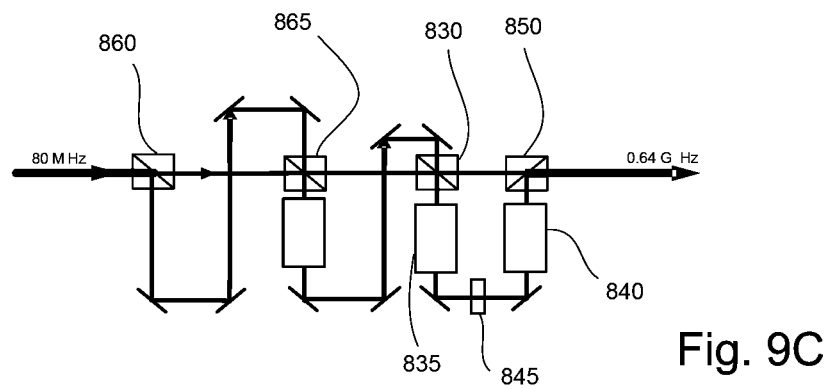
Figure 9D:
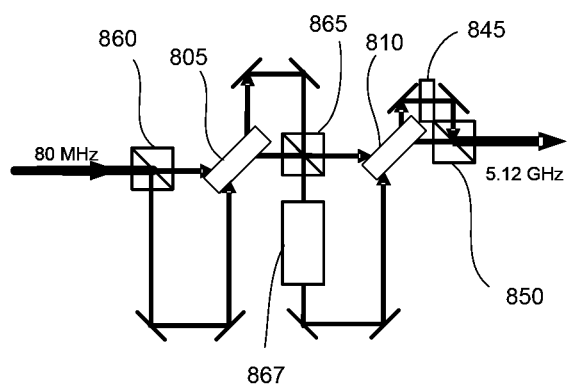

Removal of various elements from the system 800 shown in FIG. 8 leads to five different test configurations, which are shown in FIGS. 9A-9E. In FIG. 9A, the system uses the pulse splitter 810 and has eight output pulses (N=8) and a minimum pulse spacing of 37 ps ($\Delta t_{min}$=37 ps). In FIG. 9B, the system uses the pulse splitter 805 and has eight output pulses (N=8) and a minimum pulse spacing of 74 ps ($\Delta t_{min}$=74 ps). In FIG. 9C, the system has eight output pulses (N=8) and a minimum pulse spacing of 1 ns ($\Delta t_{min}$>1 ns) but the system lacks any pulse splitters and uses only beam splitters 860, 865, and 830. In FIG. 9D, the system has 64 output pulses (N=64) and a minimum pulse spacing of 37 ps ($\Delta t_{min}$=37 ps). And, in FIG. 9E (as in FIG. 8), the system has 128 output pulses (N=128) and a minimum pulse spacing of 37 ps ($\Delta t_{min}$=37 ps). The power throughputs can be greater than about 90%, 50%, and 35% for 8×, 64×, and 128× pulse splitters, respectively.

Figure 9E:
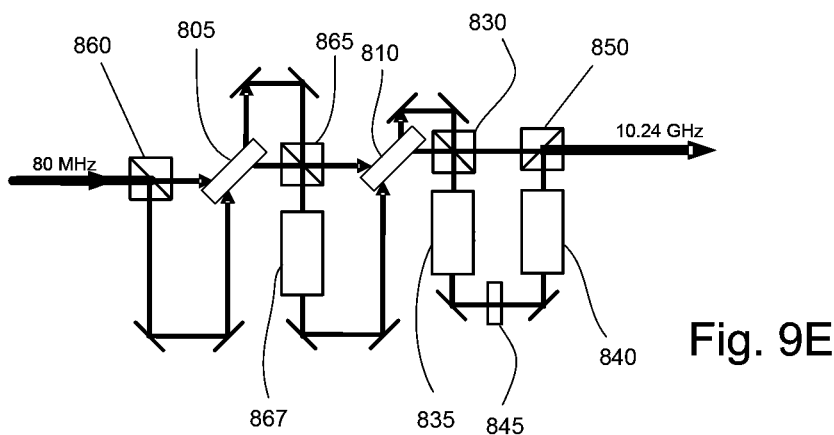
Figure 10:
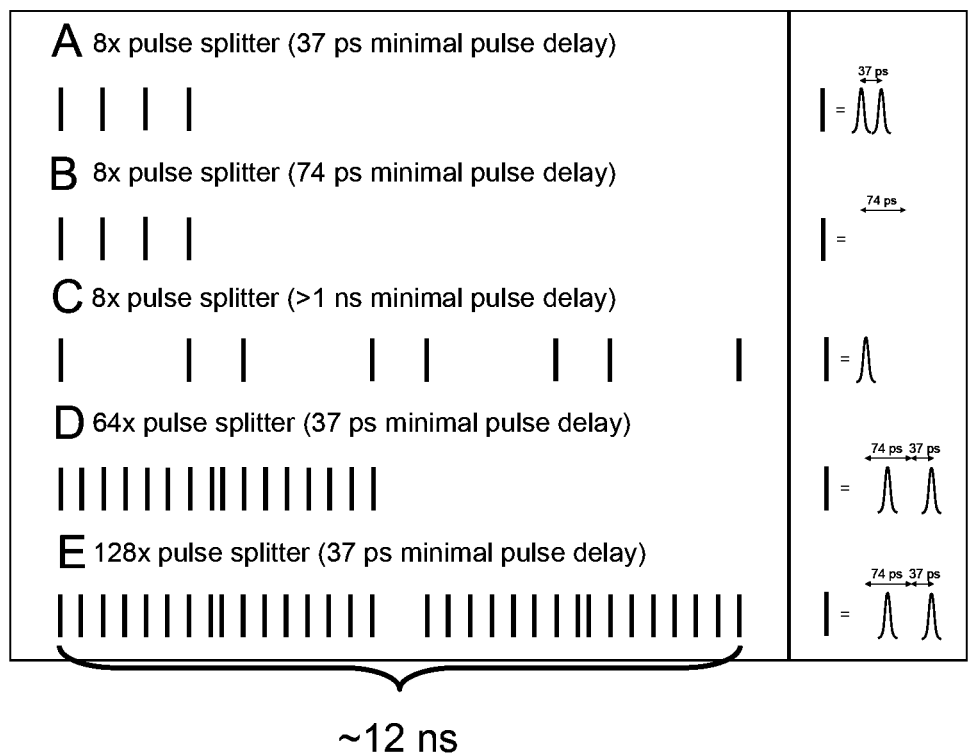
FIGS. 10A-10E are diagrams showing timing of output pulses from the pulse splitters of, respectively, FIGS. 9A-9E.

Referring to FIG. 10, temporal sequences of pulses resulting from each of the configurations shown in FIGS. 9A-9E, respectively, are shown. Thus, temporal sequence A corresponds to FIG. 9A, temporal sequence B corresponds to FIG. 9B, temporal sequence C corresponds to FIG. 9C, temporal sequence D corresponds to FIG. 9D, and temporal sequence E corresponds to FIG. 9E.

To explore the benefits of pulse splitting, the system of FIG. 8 was used in conjunction with an 80 MHz Ti:Sapphire laser (Coherent Inc., Chameleon) tuned to 910 nm and a commercial 2PFM (Prairie Technologies Inc., Ultima) equipped with a 60×, 0.9 NA water immersion objective (Olympus, LUMPlanFI/IR) to image fixed mouse cortical brain slices expressing cytosolic GFP in a subset of neurons.

Referring to FIGS. 11A-11I, in the first experiment, images were taken with the pulse splitter system 800 (images in FIGS. 11A and 11D) and without the pulse splitter system 800 (images in FIGS. 11B and 11E) in its 64 pulse configuration (FIG. 9D). Identical energies of about 0.75 pJ/pulse in the two cases were insured by delivering 64× more average power to the sample when the pulse splitter system 800 of FIG. 9D was used. Corresponding comparative line profiles (graphs shown in FIGS. 11C, 11F, and 11I) along the arrows shown at left images (in FIGS. 11A, 11D, and 11G) and center images (FIGS. 11B, 11E, and 11H) (15 pixel averages; orange or bottom in graph is with the splitter system, and gray or top in graph is without splitter system). Green arrows which are found in the left images of FIGS. 11A, 11D, and 11G indicate small neuronal processes that were more readily detected with pulse splitting. Measurement conditions of pulse splitting ratio (N), pixel dwell time, and average power at the sample are: for images in FIGS. 11A and 11D: 64×, 0.4 ms, 3.9 mW; for images in FIGS. 11B and 11E: none, 25.6 ms, 0.06 mW; for the image in FIG. 11G: 128×, 0.4 ms, 12.3 mW; and for the image in FIG. 11H: none, 40.4 ms, 0.11 mW. The scale bars shown in the lower left portions of the images are: 20 mm in images of FIGS. 11A, 11B, 11G, and 11H; and 2 mm in images of FIGS. 11D and 11E.

In the limit where the pulse energy delivered per pixel is sufficiently low and the concentration of green fluorescent protein (GFP) is sufficiently high for neither saturation to occur nor bleaching to be significant, a 64× increase in signal rate should be observed with the splitter system 800 of FIG. 9D provided that the output energy of each sub-pulse with the splitter system 800 is the same as the energy of each pulse without the splitter system 800. Comparable signals were obtained in images of FIGS. 11A and 11D and in images of FIGS. 11B and 11E, even though the imaging speed of 0.4 µs/pixel with the splitter system 800 (in images of FIGS. 11A and 11D) was 64 times faster than that without the splitter system 800 (in images of FIGS. 11B and 11E). This also provides indirect confirmation that the pulse splitter (and the system 800) produced pulses of approximately equal intensity.

Tests with a 128× splitter system (as in FIGS. 8 and 9E) yielded proportionally larger gains. For example, compare the image shown in FIG. 11G, which is an image taken with the splitter system of FIGS. 8 and 9E, to the image shown in FIG. 11H, which is an image taken without the splitter system of FIGS. 8 and 9E.

Another benefit of such fast imaging speeds is that less time exists for the integration of background arising from ambient light, so that small features yielding weak intrinsic signals such as dendrites and dendritic spines (as shown in images of FIGS. 11D and 11E) are easier to identify (see, for example, the green arrows shown in graphs of FIGS. 11C and 11I). Note the similarity in the resolution with and without the pulse splitter (images of FIGS. 11D and 11E and the graph shown in FIG. 11F), which indicates that the pulse splitter system was effective in producing spatially overlapped, co-propagating sub-pulses.

Pulse splitting reduces 2PFM photobleaching in fixed brain slices. For many nonlinear optical processes, including 2PFM, photoinduced bleaching and damage increases even more rapidly with increasing excitation intensity I than does the signal generated. A simple model suggests that, in such cases, pulse splitting can be used to reduce the rate of photobleaching and photodamage at a given signal level. Thus, consider a nonlinear process of signal $S \propto I^\alpha$ and damage $D \propto I^\beta$, where β>α>1. The signal $S_1$ generated by one pulse equals the signal $S_N$ generated by an N-pulse splitter when $I_1^\alpha = N(I_N)^\alpha$, or equivalently, $I_N = N^{-1/\alpha} I_1$, where $I_1$ and $I_N$ are the respective pulse intensities. In this limit, the photodamage $D \propto N(I_N)^\beta$ with N pulses is reduced to $N^{1-\beta/\alpha}$ times the damage $D_1$ with a single pulse. To obtain the same signal rates in the two cases, the N pulses are delivered at N times the original repetition rate, requiring an average power at the sample greater by a factor of $N^{1-1/\alpha}$.

Referring to FIGS. 12A-12C, to test this model, 2PFM line scans were performed with and without the pulse splitter (for example, the pulse splitter system 800) in neighboring regions of the same GFP-labeled soma within a fixed brain slice, and the rate of decay of the fluorescence signal was recorded. A fixed brain slice was used for these initial measurements to avoid complications in the quantitative analysis of photobleaching caused by GFP diffusion. All five splitter configurations in FIGS. 9A-9E were tested, covering output pulse numbers (or splitting ratios) of N=8 (FIGS. 9A-9C), N=64 (FIG. 9D), and N=128 (FIG. 9E). The average power $P_N$ required to achieve a constant signal rate scaled as the square root of N (FIG. 12A), as expected for two-photon MPFM (that is, $N^{1-1/\alpha}=\sqrt{N}$ for $\alpha=2$). This provided further indirect evidence of the uniformity of the pulse intensities provided by the pulse splitter system 800. These results conformed the $\sqrt{N}$ dependence expected of 2PFM (dashed line) in FIG. 12A.

In FIG. 12B, the graph shows typical data of the photobleaching signal versus time (the fluorescence over time relative to the fluorescence at time t=0), with 128× splitting (shown in the green or top set of data) and without 128× splitting (shown in the gray or bottom set of data). To measure the photobleaching rates accurately, a single exponential decay model was insufficient, and thus a double-exponential decay formula, $S=S_0+S_1 e^{-t/T_1}+S_2 e^{-t/T_2}$, was used to fit the data and is shown as the black line through the data of FIG. 12B. The shorter decay time $T_1$ describes the precipitous drop of fluorescence intensity observed at the beginning of the excitation, and $T_2$ depicts the bleaching on a longer time scale. For the green or top curve, the shorter decay time $T_1=45$ s and the longer decay time $T_2=109$ s. For the gray curve or bottom curve, $T_1=11$ s and $T_2=53$ s.

The ratio of the decay time with the splitter system 800 to that without was measured for both $T_1$ and $T_2$ in all five splitter systems shown in FIGS. 9A-9E, and the results are summarized in FIG. 12C. Average power was about 1 mW at the sample without the splitter system 800, and was about $\sqrt{N}$ mW using the splitter system. Error bars represent standard deviations inferred from multiple measurements (N>5). The values of $\beta$ are derived from these ratios and reflect the exponential dependence of the bleaching of fixed GFP on intensity (that is, the photodamage $D \propto I^\beta$).

In every configuration and on both time scales ($T_1$ and $T_2$), the rate of photobleaching at constant signal was reduced by inclusion of the splitter system. The largest gains occurred for $T_1$ (for example, greater than 4× with the 128× splitter), a fortuitous result considering that the fast photobleaching component dominates most 2PFM imaging applications at typical pixel dwell times. Furthermore, both $T_1$ and $T_2$ continued to improve with increasing N up to the largest value tested (N=128) suggesting that additional gains can be obtained with even larger splitting numbers (where the number of output pulses N for every input pulse increases to above 128).

A concern during the design of the testing experiment was that pulse splitters having sub-pulse separations (Δt) significantly shorter than the about the 3 ns fluorescence lifetime of GFP might actually result in much faster photobleaching than the laser alone, due to the possibility that 2PFM bleaching is dominated by the absorption of additional photons from molecules already in the excited state. However, the relative independence of the bleaching ratio for both $T_1$ and $T_2$ when 8× splitters of Δt=37 ps, 74 ps, and greater than 1 ns were used suggests that this concern is not warranted for the power levels and GFP concentration used in this study. Consequently, it should be feasible to develop pulse splitters having significantly higher splitting ratios (that is, the ratio of the number of output pulses, N, to the number of input pulses which is typically 1), since comparatively small (about 10-50 ps) pulse separations Δt can be used, leading to large values of N before GDD-driven pulse broadening becomes significant.

Given the results in FIG. 12C, the relationship $D_N/D_1=N^{1-\beta/\alpha}$ from above, and the fact that $\alpha=2$ for 2PFM, it is possible to estimate the exponent $\beta$ that dictates the intensity dependence of the bleaching (that is, $D \propto I^\beta$) for both the fast and slow bleaching components and under all five splitter system scenarios shown in FIGS. 9A-9E. The ten values, shown in FIG. 12C, vary between 2.2 and 2.6. The fact that these data were obtained from fixed GFP-labeled samples may explain why the values derived here differ from those reported elsewhere.

More examples of applications using the pulse splitters and systems described above are detailed below.

Pulse splitting reduces photobleaching in living C. Elegans larvae. To assess if different photobleaching mechanisms predominate for fluorescence in living vs. fixed specimens, the effect of pulse splitting on GFP photobleaching in muscle cells of C. Elegans strand PD4251 was also measured. C. Elegans larvae were paralyzed using 50 mM 2,3-butanedione monoxime (BDM) and held stationary on 2% agar. Repeated line scans were performed over individual muscle cells with and without a 64× pulse splitter system (such as the system shown in FIG. 9D) until the fluorescence signal was largely depleted in each case. An average power 8× higher was used with the pulse splitter system to yield similar signal rates in the two cases.

As shown in FIGS. 13A-D, images of each muscle cell were taken before (at t=0) and after bleaching (at t>0). The normalized photobleaching curves measured from four cells under each experimental condition are shown in FIG. 13E. FIGS. 13A-13E show the effect of 64× pulse splitting on in vivo photobleaching within a GFP-labeled C. Elegans larva: with muscle cells before (FIGS. 13A and 13C) and after (FIGS. 13B and 13D) GFP photobleaching. Cells subjected to bleaching both with (FIGS. 13C and 13D) and without (FIGS. 13A and 13B) pulse splitting are marked with dashed white curves. FIG. 13E shows normalized photobleaching curves (the 2PFM fluorescence signal) obtained by repeated line scans over single muscle cells, fit with single exponential decay curves. The curves are "normalized" by defining the signal as one unit at the start of the first scan on a given cell. As the cell is line scanned more times, the fluorescence signal drops due to bleaching, as shown in these curves. However, the splitter signal drops less rapidly with repeated scans, indicating less photobleaching with the pulse splitting. The curves obtained from the cells in FIGS. 13A and 13C are labeled with gray and green asterisks, respectively. The scale bars are 1 micron.

Because of the differences in cell size and GFP expression level, both the initial 2PFM signal (that is, the signal at the initial time the laser is directed to the sample) and photobleaching dynamics varied from cell to cell.

The photobleaching curves in C. Elegans from FIG. 13E, except before normalization, are also shown with (FIG. 14A) and without (FIG. 14B) a 64× pulse splitter. The initial 2PFM signal (at time 0) measured with (FIG. 14A) and without (FIG. 14B) pulse splitting was comparable and fell within a similar range.

The normalized photobleaching curves in FIG. 13E clearly demonstrate the benefits of pulse splitting: a GFP-labeled cell was still visible after 120 seconds with splitting (as shown in FIG. 13D), but another GFP-labeled cell was completely bleached after only 50 seconds without splitting (as shown in FIG. 13B).

In contrast to the fixed slice measurements, each in vivo photobleaching curve could be well-fit to a single exponential decay. The average photobleaching rate with 64× pulse splitting decreased by about 9-fold, from which a bleaching exponent $\beta \approx 3$ can be inferred, in agreement with previous GFP photobleaching experiments in live cells. Thus, compared to the fixed GFP case in FIGS. 12A-12C, the benefit of pulse splitting is much larger in living tissue, likely due to the higher concentration and mobility of oxygen in living specimens. These results also suggest that the effect of heating due to linear absorption on photobleaching in *C. Elegans* is minimal, since pulse splitting at an average power of 43 mW led to less bleaching than an average power of 5.5 mW without splitting.

Pulse splitting using the pulse splitters described above reduces photodamage in functional $Ca^{2+}$ imaging of hippocampal neurons in acute brain slices. A particularly important application of 2PFM in neuroscience is imaging of neural activity using $Ca^{2+}$ indicators. In this application, the $Ca^{2+}$ indicator concentration is sufficiently high and its diffusion sufficiently fast that photodamage affects experiments more than photobleaching. During a typical experiment, the basal fluorescence level F increases with exposure time, and $\Delta F/F$, the relative fluorescence intensity change upon neuronal activity, decreases with time. Prolonged exposure also often leads to severe morphological changes, such that the viability of dendrites and spines undergoing measurement ultimately limits the quantity and quality of the collected traces. Here again photodamage is known to have a higher than second order dependence on excitation intensity, so pulse splitting should prove beneficial.

To test this, we performed $Ca^{2+}$ imaging experiments on CA1 pyramidal neurons in 400 μm thick acute rat hippocampal slices at physiological temperature. Neurons were filled with 200 μM Oregon Green BAPTA-1 using whole-cell patch-clamp pipettes. To ensure uniform filling and excitation of proximal dendrites access resistance was kept minimal, a ten to fifteen minute filling time was given before recording was initiated, all recordings were limited to dendritic regions within 150 μm of the soma and separate dendrites within the same focal plain were used for comparison. Two back-propagating action potentials were induced by somatic current injection (700 pA, 10 ms) at 6 s intervals (0.17 Hz) and the $Ca^{2+}$ transient in dendrites and spines was detected by rapid line scans (512 linescans at 333 Hz) using 830 nm excitation. We chose the percentage fluorescence change $\Delta F/F$ as the metric of photodamage, and measured the dependence of $\Delta F/F$ on accumulated exposure time both with and without a 64× pulse splitter.

FIGS. 15A-15E show the effect of 64× pulse splitting on photodamage during Ca2+ imaging of CA1 pyramidal neurons injected with Oregon Green BAPTA-1. The scale bars are 1 μm in FIG. 15A and 5 μm in FIGS. 15D and 15E.

FIG. 15A shows the temporal evolution of $\Delta F/F$ from two dendritic branches of a single neuron in response to repeated action potential initiation, one measured with a 64× splitter system (the top circles) and one without (the bottom circles). Basal fluorescence images of the two branches taken at various times are also shown as insets in FIG. 15A with the 64× splitter system images being shown above the graph and the images without the splitter system being shown below the graph. Average powers of 60 mW and 5.7 mW post objective were used with and without the 64× splitter system, respectively. The power used with the 64× pulse splitter system was chosen intentionally high (for example, 60 mW>$\sqrt{64}$×5.7=45.6 mW) and yielded a higher basal fluorescence signal, as shown in FIG. 16A. Although this skews the photodamage comparison in favor of the no splitter scenario, the pulse splitter still drastically reduced photodamage.

Without pulse splitting (the gray and bottom circles shown in FIG. 15A), $\Delta F/F$ decreased rapidly after about 75 s exposure (50 traces), and after 120 traces, the basal fluorescence increased about seven-fold (inset images with gray borders below the graph of FIG. 15A), while $\Delta F/F$ dropped to 10% of its original value. At this point, the experiment had to be terminated to prevent killing the entire dendrite. In comparison, with the 64× pulse splitter system, the basal fluorescence increased much more slowly (insets with green borders above the graph of FIG. 15A): after over 700 s exposure (500 traces), $\Delta F/F$ dropped to only half of its original value. Defining the $Ca^{2+}$ imaging "lifetime" as the number of traces required for $\Delta F/F$ to decrease by one-half, we find that a 6× gain in lifetime is afforded by the use of a 64× splitter system (such as the splitter system shown in FIG. 9D), despite the higher initial basal signal we used.

Referring to FIG. 15B, $\Delta F/F$ was measured by taking longer traces (6.28 s traces every 17 s) and using higher average powers (66 mW with the 64× splitter system and 5.7 mW without the splitter system). Referring to FIG. 15C, $\Delta F/F$ was measured by using higher average powers of 100 mW with the 64× splitter system and 12.6 mW without the splitter system. Both with and without pulse splitting, higher average power compared to FIG. 15A led to faster photodamage, as expected.

FIGS. 16A-16C show $Ca^{2+}$ transient traces at the beginning of each series of traces used to measure photodamage during $Ca^{2+}$ functional imaging (FIGS. 15A-15C). Average powers are: in FIG. 16A, 60 mW with 64× splitter, 5.7 mW without; in FIG. 16B, 66 mW with 64× splitter, 9 mW without; and in FIG. 16C, 100 mW with 64× splitter, 12.5 mW without. Considerably more signal was obtained in FIG. 16A with the splitter, due to the use of more than 8× higher average power. Given similar basal fluorescence (FIGS. 16B and 16C), pulse splitting always improved the $Ca^{2+}$ imaging lifetime, with more dramatic gains occurring at increasingly high power (greater than about 10× in FIG. 15B and greater than about 20× in FIG. 15C).

In FIGS. 15D and 15E, basal fluorescence images are shown, taken before and after $Ca^{2+}$ imaging of the two sister branches used to obtain FIG. 15B. After 10 traces without pulse splitting, the upper branch showed significant damage, as indicated by its much elevated basal fluorescence (orange arrows, in FIGS. 15D and 15E). After two more traces, a brightly fluorescent vesicular structure appeared along the branch (inset, in FIG. 15E). In contrast, with pulse splitting, the elevation of basal fluorescence in the lower branch was only moderately higher even after 80 traces, (green arrows, in FIGS. 15D and 15E) and $\Delta F/F$ was still above half maximum. In line with the *C. Elegans* measurements (shown in FIGS. 13A-13E), damage due to heating by linear absorption did not appear to be significant up to 100 mW when the 64× pulse splitter was used.

The results above demonstrate the efficacy of pulse splitting for enhancing signal and reducing photobleaching and photodamage in 2PFM, as shown in the imaging apparatus of FIG. 1. The same principle that is shown in FIG. 1 can be applied to other multi-photon imaging methods, including those based on second harmonic generation (SHG), sum frequency generation, and coherent anti-Stokes Raman scattering (CARS). The microscope used in SHG and CARS is very similar to that shown in FIG. 1. For CARS, two input beams at different frequencies are used. Therefore, the apparatus 100 would include a plurality of pulsed laser sources 105. The pulse splitters 112 can be used simultaneously on a plurality of pulsed laser beams 107 at different wavelengths. Moreover, the benefits of enhancing signal and reducing photo damage can be found when the pulse splitters 112 are applied to linear optical phenomena such as linear light scattering.

Another possible, advantage is that the pulse splitter spreads the excitation energy across many time points within the original repetition period of the laser, whereas pulse broadening methods still concentrate the energy of each original pulse in a single, albeit lengthened, pulse. Damage mechanisms based on ultrafast excited state kinetics may therefore be eliminated or significantly reduced when using the splitter system due to the fact that the time between sub-pulses is greater than the molecular excited state relaxation time.

To prepare the fixed brain slices used in the tests described herein, C57B16 mice were injected with AAV2/1-GFP virus at postnatal day 13 to 15. Fourteen days later, animals were sacrificed and the brains were extracted. Brains fixed overnight in 4% paraformaldehyde were washed three times with phosphate buffer and then cut into 60 μm thick sections using a vibratome (Leica, VT1000S). For long-term storage, such sections were mounted in Vectashield (Vevtor Laboratories).

To prepare the hippocampal brain slices used in the tests described herein, transverse hippocampal slices (400 μm-thick) were prepared from 8 to 12-week old Sprague Dawley rats as previously described. Rats were given a lethal dose of ketamine and xylazine, perfused through the ascending aorta with an oxygenated solution just before death and decapitated. Hippocampal CA1 pyramidal cells were visualized using an Olympus BX-61 microscope equipped with differential interference contrast optics under infrared illumination. Experiments were performed at physiological temperature (34-36° C.) in ACSF containing the following (in mM): NaCl 125, KCl 3, $NaHCO_3$ 25, $NaHPO_4$ 1.25, $CaCl_2$ 1.3, $MgCl_2$ 1, and glucose 25; and was saturated with 95% $O_2$ and 5% $CO_2$. Current-clamp whole-cell recordings (somatic membrane voltage $V_m$=−65 mV) from somata were performed using a Dagan BVC-700 amplifier in the active bridge mode, filtered at 3 kHz and digitized at 50 kHz. Patch pipettes had a resistance of 2-4 MΩ when filled with a solution containing (in mM): K-methylsulphate 120, KCl 20, HEPES 10, NaCl 4, MgATP 4, Tris 2, GTP 0.3, phosphocreatine 14 (pH=7.25). The series resistance was between 8-15 Ma Neurons were filled with 200 μM Oregon green BAPTA-1 (OGB-1) (Molecular Probes, Eugene, Oreg., USA) and imaged using a water immersion lens (60×, 0.9 NA, Olympus, Melville, N.Y., USA). To allow for diffusional equilibration of the indicators, cells were loaded with the dye for at least 10 min before the start of experiments. In all cells two action potentials were initiated by a brief current injection into the soma (700 pA for 20 ms).

The GFP expressing C. Elegans Larvae were prepared as follows. C. Elegans was grown on agar plates spread with E. Coli bacteria. Larvae were transferred onto 2% agarose gel, paralyzed by 50 mM 2,3-butanedione monoxime (BDM), and covered with a cover glass for imaging.

Experiments were performed on a commercial 2PFM microscope (Prairie Technologies, Ultima) equipped with a 60×, 0.9NA water immersion objective (Olympus, LUMPlanFI/IR). Laser power was measured after the objective and controlled by a Pockels cell (Conoptics, Model 302). Photobleaching line scan measurements were carried out at 2 ms per 1.6 mm line. The GFP imaging and bleaching measurements were performed at a wavelength of 910 nm, whereas the calcium imaging experiments were performed at 830 nm.

All the above features can be combined with one another in any desired manner. Other aspects, advantages, and modifications are within the scope of the following claims.

In other implementations, the pulse splitter 200 discussed above is designed in a non-planar geometry, for example, an annular geometry in which the reflecting surfaces 205, 210 are rolled into each other to form annular first and second regions 215, 220. In other implementations, the reflecting surfaces 205, 210 can be multilayer dielectric films.

In other implementations, the pulse splitter 200 can be designed such that the reflecting surfaces 105, 110 are non-parallel with each other. In this way, the sub-pulses 250, 252 and 254, 256 would diverge from each other as they exit the pulse splitter 200, thus resulting in more than one focus at the sample 115 to be imaged and creating a multi-focal imaging apparatus.

Figure 17:
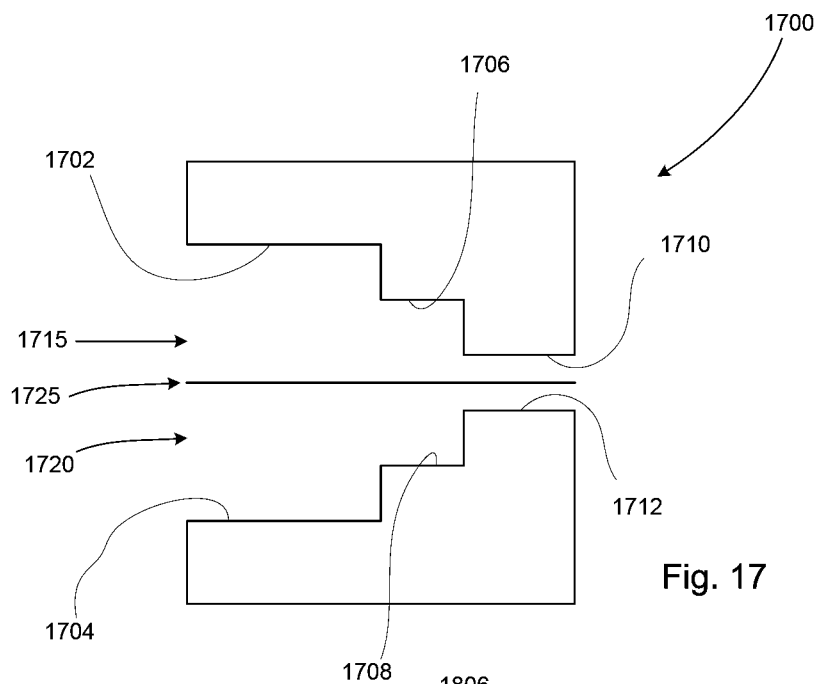
FIGS. 17 and 18 are top cross-sectional diagrams of pulse splitters that can be used in the imaging apparatus of FIG. 1.
Figure 18:
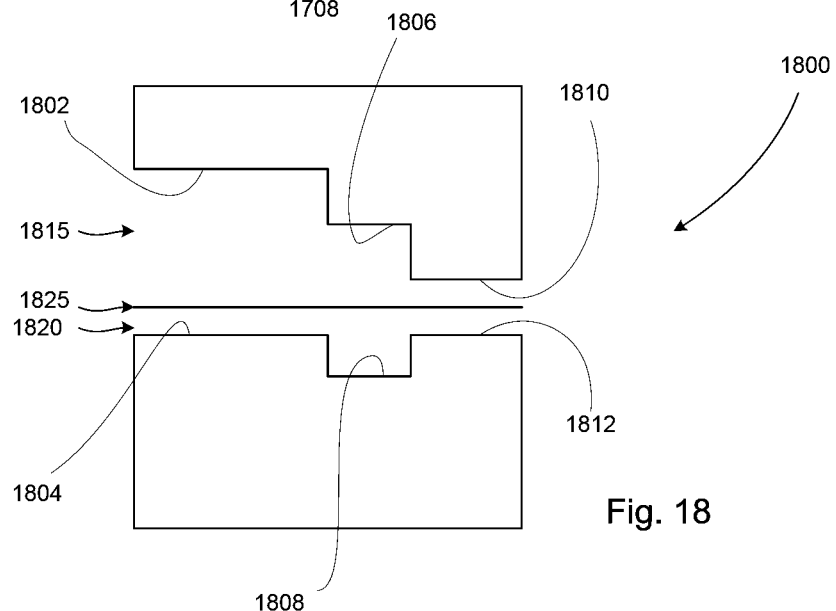

Referring to FIGS. 17 and 18, a pulse splitter 1700 or 1800 can be designed with more than one pair of reflecting surfaces. In these designs, the pulse splitter 1700 or 1800 includes three pairs of reflecting surfaces, with the distance between each pair being distinct from the distance between each of the other pairs in the pulse splitter. For example, the pulse splitter 1700 includes three pairs of reflecting surfaces, with surfaces 1702, 1704 facing each other, surfaces 1706, 1708 facing each other, and surfaces 1710, 1712 facing each other. First and second regions 1715, 1720 fill the space between the pairs of reflecting surfaces and an interface 1725 is between the first and second regions 1715, 1720, as was discussed above. Similarly, the pulse splitter 1800 includes three pairs of reflecting surfaces, with surfaces 1802, 1804 facing each other, surfaces 1806, 1808 facing each other, and surfaces 1810, 1812 facing each other. First and second regions 1815, 1820 fill the space between the pairs of reflecting surfaces and an interface 1825 is between the first and second regions 1815, 1820, as was discussed above.

Figure 19:
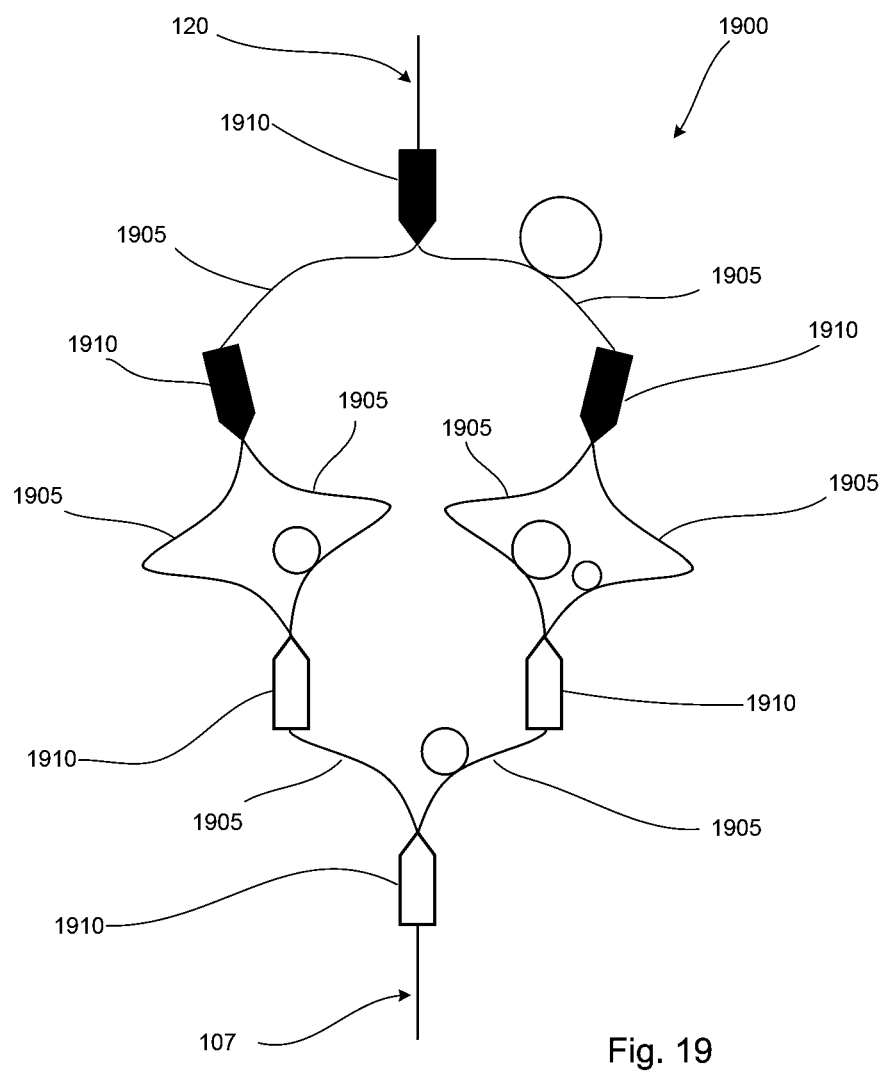
FIG. 19 is a diagram of a pulse splitter that uses optical waveguides and that can be used in the imaging apparatus of FIG. 1.

Referring also to FIG. 19, in another implementation of the pulse splitter 112, a pulse splitter 1900 is designed with a plurality of optical fibers 1905 that can be of varying lengths, one or more fiber splitters 1910, and one or more fiber couplers 1915. Each fiber splitter 1910 splits its input pulse (including the input pulse of the laser beam 107) into sub-pulses. Intermediate fibers 1905 (those between the fiber splitters 1910 and the fiber couplers 1915) introduce different time delays for each sub-pulse because they have differing lengths. The fiber couplers 1915 recombine the sub-pulses from the fibers 1905 into a single output beam 120. In another implementation, optical waveguides can be used instead of the fibers 1905 and the waveguides could be created monolithically via microfabrication on a flat substrate, although dispersion may prove challenging, particularly at the pulse splitting and re-combining sections. Dispersion in the pulse splitter 1900 might be reduced by using hollow core photonic bandgap fibers as the fibers 1905.

What is claimed is:

1. An apparatus comprising:
a pulsed laser source that produces a pulsed laser beam at an input repetition rate and an input pulse power;
a passive pulse splitter that receives the pulsed laser beam and outputs a signal including a plurality of sub-pulses for each input pulse of the pulsed laser beam, wherein the sub-pulses have a repetition rate that is greater than the input repetition rate and at least two of the sub-pulses have power less than the input pulse power;
a sample accommodating structure configured to accommodate a sample placed in the path of a sample beam that is formed from the beam that exits the pulse splitter; and
a detector that receives a signal of interest emitted from a sample accommodated by the sample accommodating structure based on the incident sample beam.

2. The apparatus of claim 1, wherein the detector receives signals of interest from a plurality of locations at the sample to form an image.

3. The apparatus of claim 1, wherein the signal of interest is multi-photon fluorescence emitted from a nonlinear sample.

4. The apparatus of claim 1, wherein the pulsed laser source is a Ti-Sapphire laser.

5. The apparatus of claim 1, wherein the pulsed laser source produces time-averaged output powers of several Watts.

6. The apparatus of claim 1, wherein the pulsed laser source operates with an input repetition rate of about 70-80 MHz, a pulse width from about 10 fs to about 2 ps, and at a 650-110 nm wavelength.

7. The apparatus of claim 1, wherein the signal of interest is a second harmonic generation signal emitted from a nonlinear sample.

8. The apparatus of claim 1, wherein the signal of interest is a signal emitted from a nonlinear sample using coherent anti-Stokes Raman scattering spectroscopy with the output signal from the passive pulse splitter.

9. The apparatus of claim 1, wherein the pulse splitter comprises one or more beam splitters and one or more beam couplers.

10. The apparatus of claim 1, wherein the pulse splitter comprises a plurality of waveguides, one or more beam splitters, and one or more beam couplers.

11. The apparatus of claim 1, wherein the pulse splitter comprises at least two different materials through which the sub-pulses travel such that each of the sub-pulses travel along different optical path lengths through different materials to cause temporal separation between each of the sub-pulses, wherein the optical path length depends on both the distance traveled through the material and the index of refraction of the material.

12. The apparatus of claim 1, wherein the pulse splitter comprises:
one or more pairs of at least partly-reflecting surfaces that face each other;
a first region between the one or more surface pairs and having a first refractive index and a first thickness;
a second region between the one or more surface pairs and adjacent the first region, and having a second refractive index that is different from the first refractive index and a second thickness that is different from the first thickness; and
a partially reflective interface between the first and second regions.

13. The apparatus of claim 1, wherein the pulse splitter outputs N sub-pulses for every one pulse input to the pulse splitter.

14. The apparatus of claim 1, further comprising a recombiner that receives the plurality of sub-pulses from the pulse splitter and recombines the sub-pulses to form the sample beam.

15. The apparatus of claim 1, further comprising a delay external to the pulse splitter and through which at least some of the output of the pulse splitter is passed.

16. The apparatus of claim 1, further comprising a motion stage to which the pulse splitter is attached such that the pulse splitter can be moved relative to the path that the laser pulses travel along.

17. The apparatus of claim 1, wherein the plurality of sub-pulses are of equal or approximately equal intensity.

18. The apparatus of claim 1, wherein the pulse splitter outputs the plurality of sub-pulses using substantially all of the available power from the pulsed laser source.

19. The apparatus of claim 1, wherein the sample beam is the beam that exits the pulse splitter.

20. A signal detection method comprising:
producing a pulsed laser beam having a repetition rate and a pulse power;
directing the pulsed laser beam into a passive pulse splitter that creates a finite number of sub-pulses for each input pulse of the pulsed laser beam and produces an output signal, wherein the sub-pulses of the output signal have a repetition rate that is greater than the repetition rate of the pulsed laser beam, wherein the powers of at least two of the sub-pulses are less than the pulse power of the pulsed laser beam;
receiving a sample signal produced from the output signal of the pulse splitter at a sample; and
receiving a signal of interest emitted from the sample due to the interaction of the sample with the pulse splitter output at a detector.

21. The method of claim 20, further comprising directing signals of interest from a plurality of locations at the sample to the detector to form an image.

22. The method of claim 20, further comprising detecting the signal of interest emitted from the sample.

23. The method of claim 22, wherein detecting the signal of interest emitted from the sample comprises detecting a fluorescence signal from the sample.

24. The method of claim 20, further comprising recombining sub-pulses from the pulse splitter output signal to form the sample signal.

25. The method of claim 20, further comprising splitting the pulse splitter output signal into at least two signals and delaying at least one of the signals relative to the other signal.

26. The method of claim 20, wherein the sample signal produced from the output signal of the pulse splitter is directed to the sample.

27. The method of claim 20, wherein the signal of interest emitted from the sample is directed to the detector.

28. The method of claim 20, wherein the sample signal is the output signal of the pulse splitter.

29. The apparatus of claim 1, wherein a plurality of sub-pulses of the outputted signal travel along a single path.

30. The apparatus of claim 29, wherein the sub-pulses of the outputted signal that travel along a single path are spatially overlapping.

31. The apparatus of claim 1, wherein the outputted signal includes a finite number of the plurality of sub-pulses.

32. The apparatus of claim 1, wherein a first plurality of pulses of the outputted signal travel along a first path and a second plurality of pulses of the outputted signal travel along a second path that is not parallel with the first path.

33. The apparatus of claim 32, further comprising a recombiner that receives the first plurality of pulses and the second plurality of pulses and combines the pulses into the sample beam traveling along a common path.

* * * * *